United States Patent
Naito et al.

(10) Patent No.: US 11,048,166 B2
(45) Date of Patent: Jun. 29, 2021

(54) PHOTOSENSITIVE COMPOUND, PHOTOACID GENERATOR AND RESIST COMPOSITION CONTAINING THE PHOTOSENSITIVE COMPOUND, AND METHOD FOR MANUFACTURING DEVICE USING THE RESIST COMPOSITION

(71) Applicant: TOYO GOSEI CO., LTD., Chiba (JP)

(72) Inventors: Michiya Naito, Chiba (JP); Masamichi Hayakawa, Chiba (JP); Yoshiyuki Utsumi, Chiba (JP)

(73) Assignee: TOYO GOSEI CO., LTD., Chiba (JP)

(*) Notice: Subject to any disclaimer, the term of this patent is extended or adjusted under 35 U.S.C. 154(b) by 212 days.

(21) Appl. No.: 16/339,014

(22) PCT Filed: Dec. 20, 2017

(86) PCT No.: PCT/JP2017/045771
§ 371 (c)(1),
(2) Date: Apr. 3, 2019

(87) PCT Pub. No.: WO2018/117167
PCT Pub. Date: Jun. 28, 2018

(65) Prior Publication Data
US 2019/0243238 A1    Aug. 8, 2019

(30) Foreign Application Priority Data
Dec. 21, 2016 (JP) .............................. JP2016-248109

(51) Int. Cl.
| G03F 7/004 | (2006.01) |
| G03F 7/039 | (2006.01) |
| G03F 7/20 | (2006.01) |
| C07C 395/00 | (2006.01) |
| C07F 11/00 | (2006.01) |
| C07C 309/12 | (2006.01) |

(52) U.S. Cl.
CPC .......... *G03F 7/0045* (2013.01); *C07C 309/12* (2013.01); *C07C 395/00* (2013.01); *C07F 11/00* (2013.01); *G03F 7/004* (2013.01); *G03F 7/039* (2013.01); *G03F 7/20* (2013.01); *G03F 7/2004* (2013.01); *G03F 7/2059* (2013.01); *C07C 2603/74* (2017.05); *G03F 7/0048* (2013.01); *Y02P 20/55* (2015.11)

(58) Field of Classification Search
CPC .............................. C07C 395/00; C07C 11/00
See application file for complete search history.

(56) References Cited

U.S. PATENT DOCUMENTS

| 3,065,160 A | 11/1962 | Levinos |
| 5,968,713 A | 10/1999 | Nozaki et al. |
| 6,013,416 A | 1/2000 | Nozaki et al. |
| 6,200,725 B1 | 3/2001 | Takechi et al. |
| 2001/0003640 A1 | 6/2001 | Takechi et al. |
| 2009/0220886 A1 | 9/2009 | Takemoto et al. |
| 2013/0137037 A1 | 5/2013 | Yamanaka et al. |
| 2019/0163055 A1* | 5/2019 | Aqad ................ G03F 7/0397 |

FOREIGN PATENT DOCUMENTS

| JP | S61-277947 A | 12/1986 |
| JP | H05-306269 A | 11/1993 |
| JP | H09-90637 A | 4/1997 |
| JP | 2001-255647 A | 9/2001 |
| JP | 2003-057822 | * 2/2003 |
| JP | 2009-221194 A | 10/2009 |
| JP | 2013-129649 A | 7/2013 |
| TW | 201235785 A | 9/2012 |
| TW | 201409168 A | 3/2014 |
| WO | 2009/087027 A2 | 7/2009 |

OTHER PUBLICATIONS

Machine translation of JP 2003-057822, published on Feb. 28, 2003 (Year: 2003).*
Knight, F.R, et al.-Noncovalent Interactions in Peri-Substituted Chalconium Acenaphthene and Naphthalene Salts: a Combined Experimental, Crystallographic, Computational, and Solid-State NMR Study, Inorg.Chem 2012, 51, p. 11087-11097, published on Sep. 24, 2012 (Year: 2012).*
Yadav, S., Raju, S., Singh, H.B., Butcher, R.J.-Selone-stabilized aryltellurenyl cations, Dalton Transactions, 2016, 45, pp. 8458-8467 (Year: 2016).*
Translation of International Search Report dated Feb. 20, 2018 of corresponding International Application No. PCT/JP2017/045771; 3 pages.
Taiwanese Office Action dated Apr. 15, 2021, in connection with corresponding TW Application No. 106144872 (18 pp., including machine-generated English translation).

* cited by examiner

*Primary Examiner* — Anca Eoff
(74) *Attorney, Agent, or Firm* — Maier & Maier, PLLC

(57) ABSTRACT

A photosensitive compound which can be suitably used for a resist composition having superior sensitivity with respect to light of short wavelength such as KrF and the like, especially to extreme ultraviolet or electron beam, superior resolution and depth of focus in lithography, and can suppress LER (line edge roughness) in fine pattern, a resist composition using the photosensitive compound, and a manufacturing method of a device is provided. A photosensitive compound including a divalent Te atom is provided.

5 Claims, No Drawings

PHOTOSENSITIVE COMPOUND, PHOTOACID GENERATOR AND RESIST COMPOSITION CONTAINING THE PHOTOSENSITIVE COMPOUND, AND METHOD FOR MANUFACTURING DEVICE USING THE RESIST COMPOSITION

TECHNICAL FIELD

Some of the embodiments of the present invention relate to a photosensitive compound. More particularly, some of the embodiments of the present invention relate to a photosensitive compound including a divalent Te atom which is suitably used for a resist composition for lithography, using as an exposure source a light of short wavelength such as KrF and the like, especially electron beam or extreme ultraviolet. Further, some of the embodiments of the present invention relate to a photoacid generator and to a resist composition containing the photosensitive compound, and to a method for manufacturing a device using the resist composition.

BACKGROUND

In recent years, manufacture of display device such as liquid crystal display (LCD) and organic EL display (OLED) and formation of semiconductor device are performed actively by taking the advantage of photolithography technique utilizing photoresist. Regarding packages and the like of such electronic parts and electronic products, light of i-line having a wavelength of 365 nm, and lights having a longer wavelength such as h-line (405 nm) and g-line (436 nm) are widely used as an active energy ray.

As the device becomes more highly integrated, demand for refining the lithography technology has become higher, and thus there is a tendency to use KrF excimer laser (wavelength of 248 nm), ArF excimer laser (wavelength of 193 nm), light of extremely short wavelength such as extreme ultraviolet (EUV, wavelength of 13.5 nm), and particle beam such as electron beam (EB) for exposure. Lithography technology using such light of short wavelength, especially the lithography technology using extreme ultraviolet (EUV) or electron beam can perform manufacture with single patterning. Accordingly, demand for resist composition showing high responsiveness to extreme ultraviolet (EUV) or to electron beam and the like is likely to increase in the future.

As the light source for the exposure shift towards shorter wavelength, higher sensitivity to the light source for the exposure is required with the resist composition, and improvement in the lithography characteristics to have resolution which enables reproduction of fine dimension pattern is required. As a resist composition which satisfies such requirement, a chemically amplified resist composition using a photoacid generator is known (Patent Literature 1).

On the other hand, in the conventional EUV lithography apparatus, power necessary to emit laser from the light source was not enough, and thus there was a limitation in enlarging the dose to efficiently generate acid from the photoacid generator in the resist composition during exposure. Accordingly, improvement in acid generation efficiency of the photoacid generator in the resist composition is required.

CITATION LIST

Patent Literature

[Patent Literature] JP H9-90637A

SUMMARY OF INVENTION

Technical Problem

In the conventional chemically amplified resist composition, it was difficult to simultaneously satisfy the characteristics of the sensitivity to KrF excimer laser, ArF excimer laser, electron beam and extreme ultraviolet (EUV), resolution, depth of focus, and pattern characteristics.

In particular, in conventional chemically amplified resist composition for electron beam or EUV and the like, absorbance of electron beam or EUV was little, and thus it was difficult to simultaneously satisfy the characteristics of the sensitivity to electron beam or EUV, resolution, depth of focus, and pattern characteristics.

Some of the embodiments of the present invention have an object to provide a photosensitive compound used for resist composition having superior characteristics such as large absorbing efficiency for light of short wavelength such as KrF, especially such as EUV or electron beam; sensitivity; resolution; and pattern performance.

Further, some of the embodiments of the present invention have an object to provide a photosensitive compound, a photoacid generator and to a resist composition containing the photosensitive compound, and to a method for manufacturing a device using the resist composition.

Solution to Problem

The inventors have conducted extensive studies to solve the afore-mentioned problems. The inventors have found that by allowing a compound having a particular metal to be contained in the resist composition as the photosensitive compound, characteristics such as large absorbing efficiency for light of short wavelength such as KrF, especially such as EUV or electron beam; sensitivity; resolution; and pattern performance can be improved, thereby leading to completion of some of the embodiments of the present invention.

That is, one of the embodiments of the present invention is a photosensitive compound including a divalent Te atom. More particularly, one of the embodiments of the present invention is a photosensitive compound having either one of a skeleton selected from an onium salt skeleton, a diazomethane skeleton, an imide skeleton and an oxime skeleton, wherein the skeleton comprises at least one Te atom containing group represented by the following formula (1).

[Chemical Formula 1]

$$*-Te-R^1 \qquad (1)$$

Here, in the formula (1), each of $R^1$ independently represents either one of a substituent group selected from the group consisting of a linear, branched, or a cyclic hydrocarbon group having 1 to 20 carbon atoms; and an aryl group having 5 to 20 carbon atoms. A part of or all of the hydrogen atoms of the hydrocarbon group and the aryl group can be substituted by a substituent group. When the hydrocarbon group includes a methylene group, a divalent hetero atom containing group can be included in the place of at least one methylene group. The aryl group can include a hetero atom in the place of at least one carbon atom in the cyclic structure. In formula (1), "*" represents a bonding portion with the skeleton.

Another embodiment of the present invention is a photoacid generator and a resist composition containing the photosensitive compound.

Another further embodiment of the present invention is a method for manufacturing a device including:
forming a resist film on a substrate by using the resist composition; exposing the resist film; and
forming a resist pattern by developing the exposed resist film.

Technical Effect

Since the photosensitive compound of one embodiment of the present invention includes a particular metal, it has increased membrane absorbance for light of short wavelength such as KrF, especially extreme ultraviolet (EUV) or electron beam, thereby achieving high ionization efficiency and increased secondary electron generation efficiency. Accordingly, the photosensitive compound is superior in sensitivity, resolution, and pattern performance.

Embodiment

Hereinafter, some of the embodiments of the present invention will be described in detail.
<1> Photosensitive Compound The photosensitive compound of one embodiment of the present invention includes a divalent Te atom.

Since the photosensitive compound includes a divalent Te atom, it has increased membrane absorbance for light of short wavelength such as KrF, especially EUV or electron beam, thereby achieving high ionization efficiency and increased secondary electron generation efficiency. Accordingly, the resist composition containing the photosensitive compound becomes highly sensitive.

The photosensitive compound can include the ones having either one of a skeleton selected from an onium salt skeleton, a diazomethane skeleton, an imide skeleton and an oxime skeleton, wherein the skeleton comprises a Te atom containing group represented by the following formula (1), for example.

[Chemical Formula 2]

$*-Te-R^1$ (1)

Here, in the formula (1), each of $R^1$ independently from each other represents either one selected from the group consisting of a linear, branched, or a cyclic hydrocarbon group having 1 to 20 carbon atoms; and an aryl group having 5 to 20 carbon atoms. Apart of or all of the hydrogen atoms of the hydrocarbon group and the aryl group can be substituted by a substituent group. When the hydrocarbon group includes a methylene group, a divalent hetero atom containing group can be included in the place of at least one methylene group. The aryl group can include a hetero atom in the place of at least one carbon atom in the cyclic structure. In formula (1), "*" represents a bonding portion with the skeleton.

The Te atom containing group can be directly bonded to the skeleton, or can be bonded via a divalent bonding group. The divalent bonding group can include a linear, branched, or cyclic divalent hydrocarbon group; an arylene group; and a group having these groups being bonded via a group containing an oxygen atom, a sulfur atom, or a nitrogen atom. The divalent hydrocarbon group can include a group transformed into a divalent group by removing one hydrogen from the hydrocarbon group of $R^1$. The arylene group can include a group transformed into a divalent group by removing one hydrogen from the aryl group of $R^1$.

The linear, branched, or a cyclic hydrocarbon group having 1 to 20 carbon atoms can include; a linear alkyl group such as methyl, ethyl, n-propyl, n-butyl, and the like; a branched alkyl group such as isopropyl, t-butyl and the like;
a cyclic alkyl group such as cyclobutyl group, cyclopentyl group, cyclohexyl group and the like; an alkenyl group in which at least one carbon-carbon single bond of the alkyl group is substituted with a carbon-carbon double bond; an alkynyl group in which at least one carbon-carbon single bond of the alkyl group is substituted with a carbon-carbon triple bond and the like.

The cyclic alkyl group other than those mentioned above can include; alkyl groups such as a spiro cyclic alkyl group such as a spiro [3,4] octyl group, a spiro bicyclopentyl group and the like; a bridged cyclic alkyl group such as a norbornyl group, a tricyclodecanyl group, a tetracyclododecanyl group an adamantyl group and the like; a condensed cyclic alkyl group having a decaline skeleton, a steroid skeleton and the like.

In the hydrocarbon group of $R^1$, $R^1$ can include in its skeleton, in place of at least one methylene group, one of a divalent heteroatom containing group selected from the group consisting of —O—, —CO—, —COO—, —OCO—, —O—CC—O—, —NHCO—, —CONH—, —NH—CO—O—, —O—CO—NH—, —S—, —SO—, and —SO$_2$—. In —NHCO—, —CONH—, —NH—CO—O—, and —O—CO—NH— and the like represented as the afore-mentioned heteroatom containing group, hydrogen atom bonded to the nitrogen atom can be substituted with an alkyl group ($R^{Sp}$) or an aryl group ($Ar^{Sp}$). $R^{Sp}$ and $Ar^{Sp}$ will be explained later.

The afore-mentioned hydrocarbon group containing a heteroatom containing group can include; an alkoxy group; an alkyl carbonyl oxy group; a hydrocarbon group having a heteroring structure such as a lactone structure, a sultone structure, a lactam structure and the like for example.

The aryl group having 5 to 20 carbon atoms can include a monovalent aromatic hydrocarbon group such as a phenyl group, a naphthyl group, an anthracenyl group, a phenanthrenyl group, an azulenyl group and the like. Here, the aryl group having 5 to 20 carbon atoms can be a monovalent aromatic heterocyclic group having a hetero atom in place of a carbon atom in the ring of the afore-mentioned aromatic hydrocarbon group. Such aromatic heterocyclic group, a monovalent aromatic heterocyclic group can include having a skeleton of furan, thiophene, pyran, chromene, thianthrene, dibenzothiophene, xanthene and the like.

The afore-mentioned hydrocarbon group and the aryl group as $R^1$ can include a substituent group. The substituent group of $R^1$ can include an alkyl group ($R^{Sp}$); an alkyl group including in its skeleton a divalent hetroatom-containing group in place of at least one methylene group of the alkyl group; an alkenyl group having at least one carbon-carbon single bond of the alkyl group substituted with a carbon-carbon double bond; an aryl group ($Ar^{Sp}$); a hydroxy group; a halogen atom and the like.

The afore-mentioned $R^{Sp}$ can include a linear, branched, or cyclic alkyl group. The afore-mentioned $Ar^{Sp}$ can include an aromatic hydrocarbon group having 12 or less carbon atoms such as a phenyl group, a naphthyl group and the like, and an aromatic heterocyclic group which can include a hetero atom in place of a carbon atom in the ring structure.

The substituent group regarding the alkyl group ($R^{Sp}$), the alkenyl group and the aryl group ($Ar^{Sp}$) can include the ones similar as the afore-mentioned alkyl group, the alkenyl group and the aryl group of $R^1$.

The substituent group of $R^1$ regarding the halogen atom can include a fluorine atom, a chlorine atom, a bromine atom and the like.

Here, the total number of carbon atoms in each of $R^1$ when $R^1$ has a substituent group is preferably 1 to 20 including the substituent group, more preferably 5 to 15, and especially preferably 6 to 10.

As the substituent group of $R^1$, an alkyl group such as a methyl group and the like, an alkoxy group, a hydroxy group, an aryl group and the like are preferable.

As the $R^1$, an alkyl group such as a methyl group, a n-butyl group and the like; and an aryl group such as a phenyl group, a naphthyl group and the like are preferable.

(Photosensitive Compound Having an Onium Salt Skeleton)

When the photosensitive compounds according to some embodiments of the present invention have an onium salt skeleton, the ones represented by the following formula (2) can be mentioned. Here, the present invention is not limited to these.

[Chemical Formula 3]

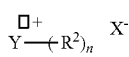

(2)

In formula (2), Y represents either one of an atom selected from the group consisting of an iodine atom, a sulfur atom, a selenium atom, and a tellurium atom. When Y is iodine atom, n is 2; and when Y is sulfur atom, selenium atom, or tellurium atom, n is 3.

$R^2$ is independently from each other selected from the same candidates for the afore-mentioned $R^1$, and at least one $R^2$ in the formula (2) has the Te atom containing group as a substituent group.

The substituent group of $R^2$ can include the ones similar to the substituent group of $R^1$.

The substituent group of $R^2$, an alkyl group can preferably include an ester group, a hydroxy group, a sulfonyl group, a fluoro group and the like.

When $R^2$ includes the Te atom containing group, preferable $R^2$ is, from the viewpoint of membrane density, solubility and the like, an aryl group having the Te atom containing group. Among the aryl group, a phenyl group having the Te atom containing group, a naphthyl group having the Te atom containing group and the like are more preferable.

When $R^2$ does not include the Te atom containing group, the preferable $R^2$ can include, from the viewpoint of solubility and the like, an alkyl group such as a methyl group, an ethyl group, a n-propyl group, an isopropyl group, a n-butyl group, a t-butyl group, a n-pentyl group, a n-hexyl group, a cyclopentyl group, a cyclohexyl group, an adamantyl group and the like; an aryl group and the like.

Two or more of $R^2$ can be bonded to each other to form a ring structure with Y, and the ring structure can include a hetero atom. Here, $Y^+$ preferably is not directly bonded with the hetero atom and is bonded with a divalent hydrocarbon group.

As the cation which is formed by two or more of $R^2$ being bonded to each other to form a ring structure with Y, the following can be mentioned for example. In the following, Y represents either one of a sulfur atom, a selenium atom and a tellurium atom. Here, $-R^3-Te-R^1$ corresponds to $R^2$ having the Te atom containing group represented by formula (1). In the following example, a cation having one Te atom containing group was shown, however, the cation can have two or more of the Te atom containing group, and the cation of the present invention is not limited to the following examples. The $R^3$ can include the afore-mentioned bonding group and the like.

The photosensitive compounds of some embodiments of the present invention preferably have two or more of the Te atom containing group represented by formula (1), since absorption of electron beam or EUV becomes high.

[Chemical Formula 4]

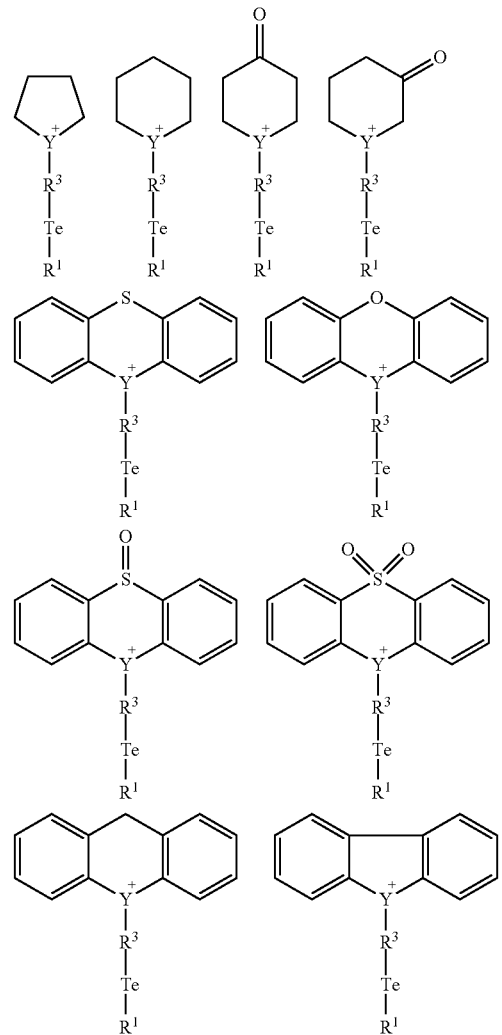

Here, an example of the afore-mentioned exemplified cation when $R^3$ is a phenylene group is shown below. In this example, a cation including one Te atom containing group represented by the formula (1) is shown, however, the cation can include two or more of the Te atom containing group, and the cation of the present invention is not limited to those shown in the following examples.

[Chemical Formula 5]

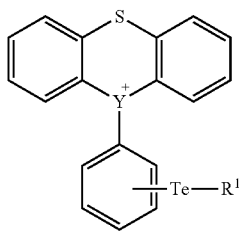
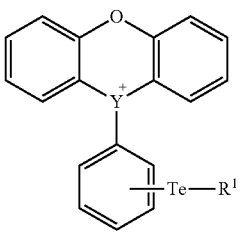
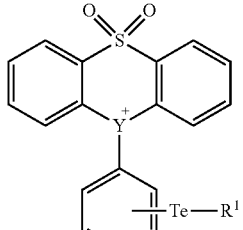
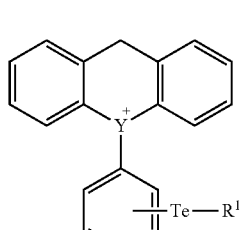
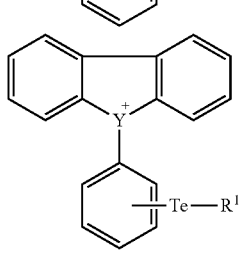

The photosensitive compound as one embodiment of the present invention is preferably an onium salt compound represented by the formula (3) in which Y is an iodine atom or the formula (4) in which Y is a sulfur atom.

The cation of the onium salt compound represented by formula (3) or (4) shows a mono-cation, however, the cation can be a poly-cation. When the cation is a poly-cation, anion is such corresponding to the poly-cation.

[Chemical Formula 6]

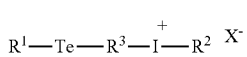 (3)

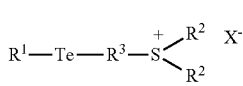 (4)

$R^1$, $R^2$, $R^3$, and X in formulas (3) and (4) are selected from the same candidates for $R^1$, $R^2$, $R^3$, and $X^-$ in the aforementioned formulas (1) and (2). Details for $X^-$ will be discussed later. As described above, —$R^3$—Te—$R^1$ corresponds to $R^2$ including the Te atom containing group as represented by formula (1). Here, $R^2$ in formulas (3) and (4) can be those having further Te atom containing groups.

A specific structure of the onium salt compound represented by formula (3) when $R^3$ is a phenylene group or a naphthylene group can include the ones shown below. In the below examples, cations including one Te atom containing group represented by formula (1) are shown, however, the cation can have two or more of the Te atom containing group, and the cation of the present invention is not limited to those shown in the following examples.

[Chemical Formula 7]

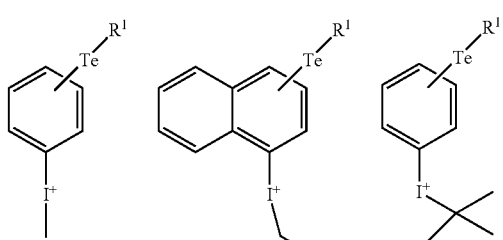

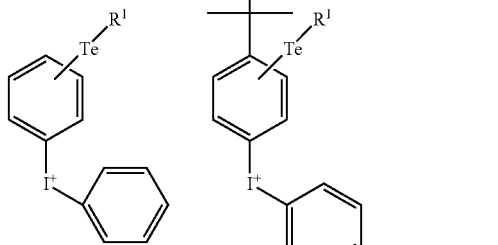

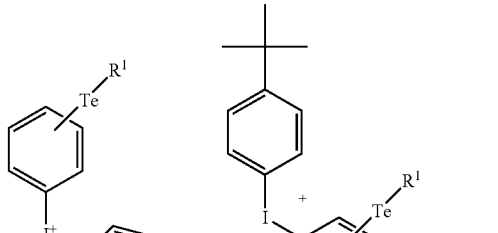

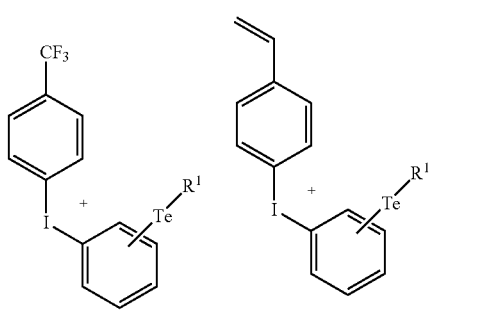

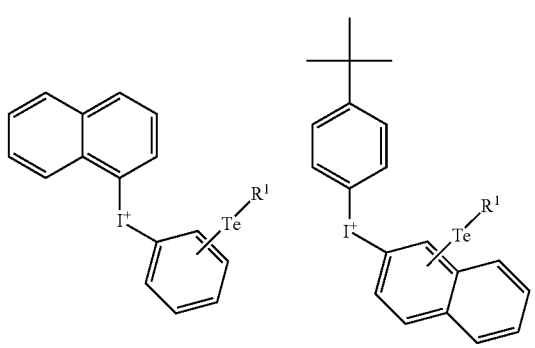

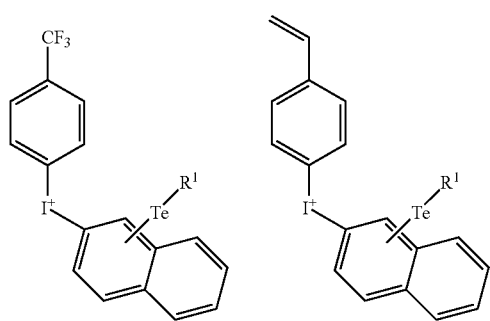
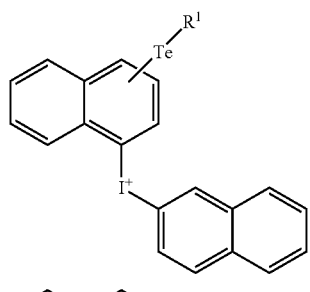
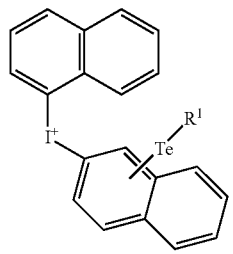
A specific structure of the onium salt compound represented by formula (4) when $R^3$ is a phenylene group or a naphthylene group can include the ones shown below. The present invention is not limited to these.
[Chemical Formula 8]
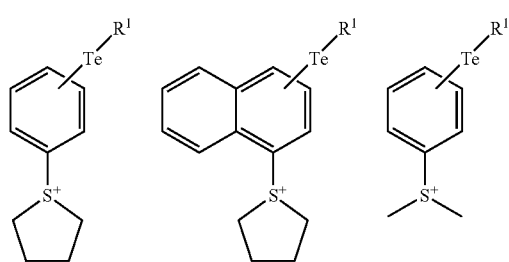
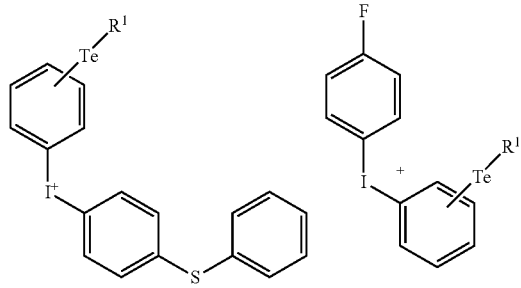

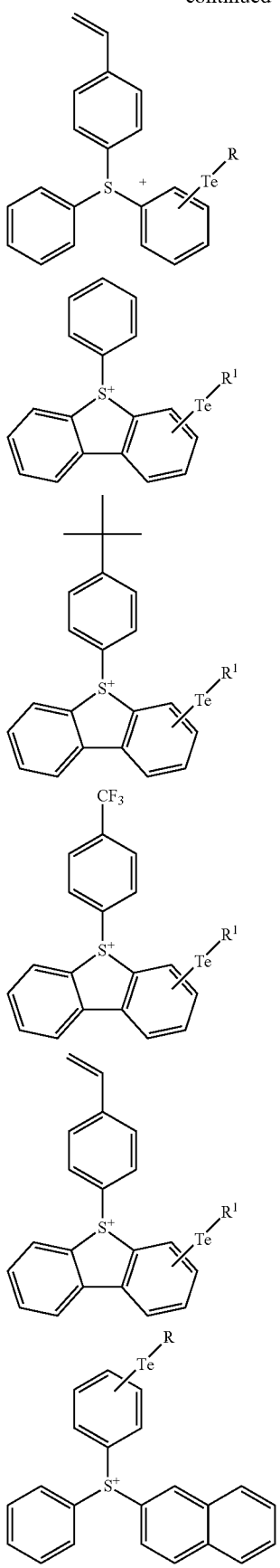

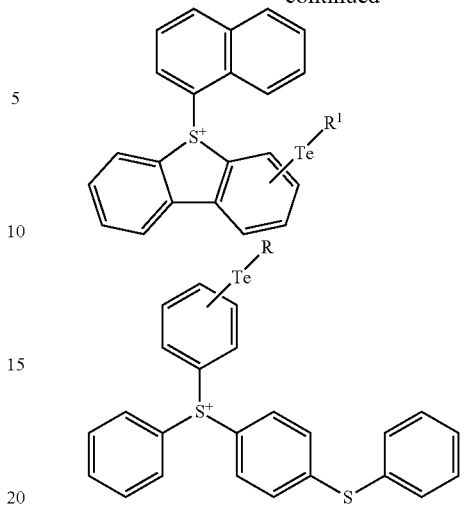

X⁻ of the onium salt compound represented by formula (2) is an anion. There is no particular limitation for the anion, and anion such as sulfonic acid anion, carboxylic acid anion, imide anion, methide anion, carbo anion, borate anion, halogen anion, phosphate anion, antimonate anion, arsenate anion and the like can be mentioned.

In more detail, anion represented by $ZA^{a-}$, $(Rf))_bPF_{(6-b)}^-$, $R^4_eBA_{(4-c)}^-$, $R^4_cGaA_{(4-c)}^-$, $R^5SO_3^-$, $(R^5SO_2)_3C^-$ or $(R^5SO_2)_2N^-$ can be preferably mentioned. Two of Rf, two of $R^4$, and two of $R^5$ can each be bonded with each other to form a ring.

Z represents a phosphorus atom, a boron atom, or an antimony atom. A represents a halogen atom (preferably a fluorine atom).

P represents a phosphorus atom, F represents a fluorine atom, B represents a boron atom, and Ga represents a gallium atom.

S represents a sulfur atom, O represents an oxygen atom, C represents a carbon atom, and N represents a nitrogen atom.

Rf is preferably an alkyl group having 80 mol % or more of its hydrogen atom substituted with fluorine atom, and the alkyl group having 1 to 8 carbon atoms is preferable. The alkyl group made into Rf by fluorine substitution can include a linear alkyl group (methyl, ethyl, propyl, butyl, pentyl, octyl and the like), a branched alkyl group (isopropyl, isobutyl, s-butyl, t-butyl and the like), a cycloalkyl group (cyclopropyl, cyclobutyl, cyclopentyl, cyclohexyl and the like) and the like. In Rf, the ratio of the hydrogen atom of the alkyl group being substituted with fluorine atom is preferably 80 mol % or more, more preferably 90% or more, and especially preferably 100%, based on the molar number of the hydrogen atom contained in the original alkyl group.

When the ratio of substitution by fluorine atom is in such preferable range, the light responsiveness of the sulfonium salt becomes further favorable. The especially preferable Rf can include $CF_3^-$, $CF_3CF_2^-$, $(CF_3)_2CF^-$, $CF_3CF_2CF_2^-$, $CF_3CF_2CF_2CF_2^-$, $(CF_3)_2CFCF_2^-$, $CF_3CF_2(CF_3)CF^-$ and $(CF_3)_3C^-$. Rf contained by the number of "b" are independent from each other, and thus they can be the same or different from each other.

$R^4$ represents a phenyl group having a part of hydrogen atoms being substituted with at least one halogen atom or electron withdrawing group. The halogen atom can include a fluorine atom, a chlorine atom, a bromine atom and the like. The electron withdrawing group can include a trifluoromethyl group, a nitro group, a cyano group and the like.

Among these, a phenyl group having one hydrogen atom substituted with a fluorine atom or a trifluoromethyl group is preferable. $R^4$ contained by the number of "c" are independent from each other, and thus they can be the same or different from each other.

$R^5$ represents an alkyl group having 1 to 20 carbon atoms, a perfluoroalkyl group having 1 to 20 carbon atoms, or an aryl group having 6 to 20 carbon atoms. The alkyl group and the perfluoroalkyl group can be either linear, branched, or cyclic group, and the aryl group can be a non-substituted group or can have a substituent group.

"a" represents an integer of 4 to 6. "b" represents an integer of 1 to 5, preferably 2 to 4, and especially preferably 2 or 3. "c" represents an integer of 1 to 4, preferably 4.

The anion represented by $ZA_a^-$ can include anions represented by $SbF_6^-$, $PF_6^-$, and $BF_4^-$.

The anion represented by $(Rf)_bPF_{(6-b)}^-$ can include anions represented by $(CF_3CF_2)_2PF_4^-$, $(CF_3CF_2)_3PF_3^-$, $((CF_3)_2CF)_2PF_4^-$, $((CF_3)_2CF)_3PF_3^-$, $(CF_3CF_2CF_2)_2PF_4^-$, $(CF_3CF_2CF_2)_3PF_3^-$, $((CF_3)_2CFCF_2)_2PF_4^-$, $((CF_3)_2CFCF_2)_3PF_3^-$, $(CF_3CF_2CF_2CF_2)_2PF_4^-$ and $(CF_3CF_2CF_2CF_2)_3PF_3^-$. Among these, anions represented by $((CF_3)_2CF_2)_3PF_3^-$, $(CF_3CF_2CF_2)_3PF_3^-$, $(CF_3)_2CF)_3PF_3^-$, $(CF_3)_2CF)_2PF_4^-$, $(CF_3)_2CFCF_2)_3PF_3^-$ and $((CF_3)_2CFCF_2)_2PF_4^-$ are preferable.

The anion represented by $R^4_cBA_{(4-c)}^-$ can include anion represented by $(C_6F_5)_4B^-$, $(CF_3)_2C_6H_3)_4B^-$, $(CF_3C_6H_4)_4B^-$, $(C_6F_5)_2BF_2^-$, $C_6F_5BF_3^-$ and $(C_6H_3F_2)_4B^-$. Among these, anion represented by $(C_6F_5)_4B^-$ and $((CF_3)_2C_6H_3)_4B^-$ are preferable.

The anion represented by $R^4_cGaA_{(4-c)}^-$ can include anion represented by $(C_6F_5)_4Ga^-$, $(CF_3)_2C_6H_3)_4Ga^-$, $(CF_3C_6H_4)_4Ga^-$, $(C_6F_5)_2GaF_2$, $C_6F_5GaF_3^-$ and $(C_6H_3F_2)_4Ga^-$. Among these, anion represented by $(C_6F_5)_4Ga^-$ and $((CF_3)_2C_6H_3)_4Ga^-$ are preferable.

The anion represented by $R^5SO_3^-$ can include those described in WO 2011/093139. As a radiation-sensitive acid generator, a sulfonic acid derivative having an anion structure represented by the following formula (a1) is preferable, however, the present invention is not limited to these.

$$R^{5a}COOCH_2CH_2CFHCF_2SO_3^- \quad (a1)$$

In formula (a1), $R^{5a}$ represents a monovalent organic group having 1 to 20 carbon atoms, which can have a substituent group. As the organic group, a group represented by the following formula having 1 to 20 carbon atoms can be preferably mentioned.

$$R^{5b}-(L-R^{5c})_n- \quad (a2)$$

In formula (a2), $R^{5b}$ is either one of a monovalent group selected from a linear, branched, or cyclic monovalent aliphatic hydrocarbon group; a monovalent aromatic hydrocarbon group; and a monovalent aliphatic heterocyclic group or a monovalent aromatic heterocyclic group having in its skeleton at least one structure selected from the group consisting of —O—, —CO—, —COO—, —OCO—, —O—CO—O—, —NHCO—, —CONH—, —NH—CO—O—, —O—CO—NH—, —NH—, —N=, —S—, —SO—, and —SO_2—.

Here, L is either one of a group selected independently from each other, from a direct bond; or from the group consisting of —O—, —CO—, —COO—, —OCO—, —O—CO—O—, —NHCO—, —CONH—, —NH—CO—O—, —O—CO—NH—, —NH—, —S—, and —CO—O—CH_2—CO—.

$R^{5c}$ is either one of a divalent group selected independently from each other, from a linear, branched, or cyclic divalent aliphatic hydrocarbon group; a divalent aromatic hydrocarbon group; and a divalent aliphatic heterocyclic group or a divalent aromatic heterocyclic group having at least one structure in its skeleton, the structure being selected from a group consisting of —O—, —CO—, —COO—, —OCO—, —O—CO—O—, —NHCO—, —CONH—, —NH—CO—O—, —O—CO—NH—, —NH—, —N=, —S—, and —SO_2—.

Here, in the afore-mentioned formula (a2), "m" is 0 or an integer of 1 to 10. When "m" is 0, $R^{5a}$ includes the hydroxyl group, and when "m" is 1 or higher, at least either one of $R^{5b}$ and $R^{5c}$ includes the hydroxyl group. "m" is preferably 0 to 5, more preferably 0 to 3.

Here, when $R^{5a}$ has a substituent group, the number of carbon atom including the number of carbon atom of such substituent group is preferably 1 to 200, more preferably 1 to 100, further preferably 1 to 30, and especially preferably 3 to 30. Further, it is preferable that $R^{5a}$ has a substituent group. That is, at least one of the hydrogen atoms of $R^{5b}$ and $R^{5c}$ is preferably substituted by the substituent group.

The substituent group which can be included in $R^{5a}$ can include a hydroxy group, a carboxy group, an alkoxy group, an acyl group, an alkoxycarbonyl group, an aryl group, an aryloxy group, a phosphino group, an alkylthio group, an arylthiol group and the like, however, the substituent group is not limited to these.

The anion represented by $R^5SO_3^-$ can include trifluoromethanesulfonic acid anion, pentafluoroethanesulfonic acid anion, heptafluoropropanesulfonic acid anion, nonafluorobutanesulfonic acid anion, pentafluorophenylsulfonic acid anion, p-toluenesulfonic acid anion, benzenesulfonic acid anion, camphorsulfonic acid anion, methanesulfonic acid anion, ethanesulfonic acid anion, propanesulfonic acid anion, butanesulfonic acid anion and the like, in addition to the anion represented by formula (a1). Among these, trifluoromethanesulfonic acid anion, nonafluorobutanesulfonic acid anion, methanesulfonic acid anion, butanesulfonic acid anion, benzenesulfonic acid anion, p-toluenesulfonic acid anion and the like can be mentioned.

The anion represented by $(R^5SO_2)_3C^-$ can include anions represented by $(CF_3SO_2)_3C^-$, $(C_2F_5SO_2)_3C^-$, $(C_3F_7SO_2)_3C^-$, $(C_4F_9SO_2)_3C^-$ and the like.

The anion represented by $(R^5SO_2)_2N^-$ can include anions represented by $(CF_3SO_2)_2N^-$, $(C_2F_5SO_2)_2N^-$, $(C_3F_7SO_2)_2N^-$, and $(C_4F_9SO_2)_2N^-$ and the like In addition, a cyclic imide having a ring structure formed by bonding portions corresponding to two $(R^5SO_2)$ with each other can also be mentioned as the anion represented by $(R^5SO_2)_2N^-$.

As the monovalent anion, perhalogenated ion ($ClO_4^-$, $BrO_4^-$ and the like), halogenated sulfonic acid ion ($FSO_3^-$, $ClSO_3^-$ and the like), sulfonic acid ion ($CH_3SO_4^-$, $CF_3SO_4^-$, $HSO_4^-$ and the like), carbonic acid ion ($HCO_3$, $CH_3CO_3^-$ and the like), aluminic acid ion ($AlCl_4^-$, $AlF_4^-$ and the like), hexafluorobismuth acid ion ($BiF_6^-$), carboxylic acid ion ($CH_3COO^-$, $CF_3COO^-$, $C_6H_5COO^-$, $CH_3C_6H_4COO^-$, $C_6F_5COO^-$, $CF_3C_6H_4COO^-$ and the like), aryl boric acid ion ($B(C_6H_5)_4^-$, $CH_3CH_2CH_2CH_2B(C_6H_5)_3^-$ and the like), thiocyanic acid ion ($SCN^-$), nitric acid ion ($NO_3^-$) and the like can be used in addition to the afore-mentioned anion.

Among these anions, sulfonic acid anion and the like are preferable.

When the photosensitive compound is an onium salt compound, an embodiment including the photosensitive compound in a resist composition as the low-molecular component can be adopted, or a polymer including the onium salt compound as a unit can be adopted. That is, the photosensitive compound represented by formula (2) can be included in the polymer as a unit by bonding with the polymer main chain at an arbitrary position of $R^2$ of the photosensitive compound. For example, when the photosensitive compound is an onium salt compound represented by formula (2), it is preferable that the photosensitive compound includes a bonding group which bonds with the polymer main chain directly or via a bonding position, in place of one H included in $R^2$. Here, when $R^2$ includes a Te atom containing group represented by formula (1), $R^2$ can include a bonding group which bonds with the polymer main chain directly or via a bonding group, in place of one H included in the Te atom containing group. When the photosensitive compound is a polymer, the polymer can be bonded with the polymer main chain directly or via a bonding group, by the anion portion, in place of the cation portion.

As the unit structuring the polymer, a unit derived from a monomer having a radical polymerizing group such as a vinyl group, an isopropenyl group, an acryloxy group, a methacryloxy group and the like is preferable. The polymer can be a polymer including another unit other than the unit corresponding to the metal-including onium salt compound. Details will be given later.

Here, when the photosensitive compound is a polymer, preferable number of carbon atoms in $R^2$ of the formula (2) is a number except for the number of carbon atoms contained in the polymer main chain.

A specific structure of the photosensitive compound represented by formula (2) can include the ones shown below. In the present invention, the photosensitive compound shown below are not limited to those shown below, including the substitution position corresponding to —Te—$R^1$.

[Chemical Formula 9]

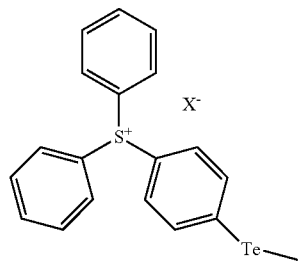

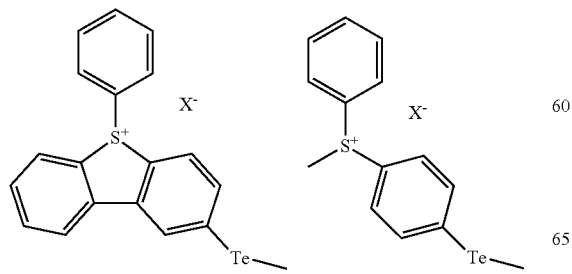

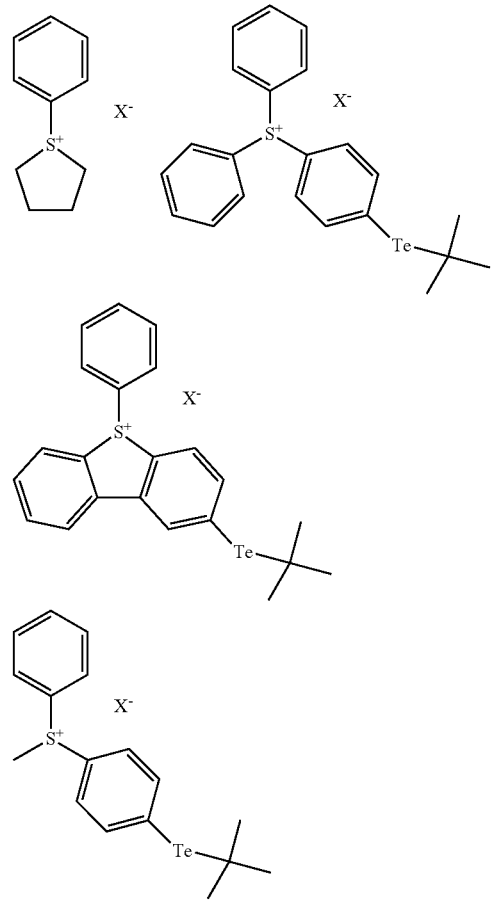

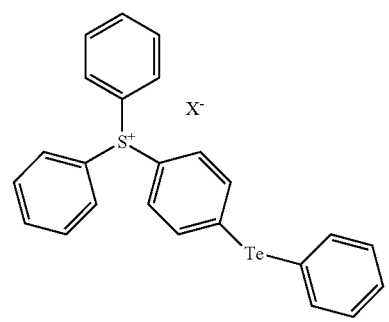

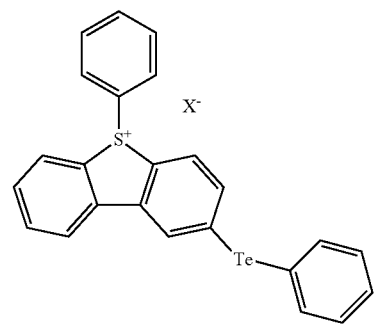

-continued
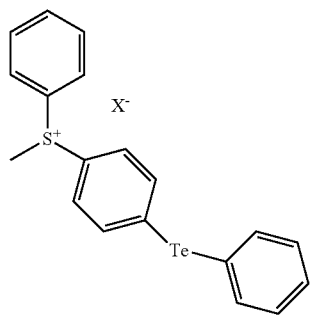
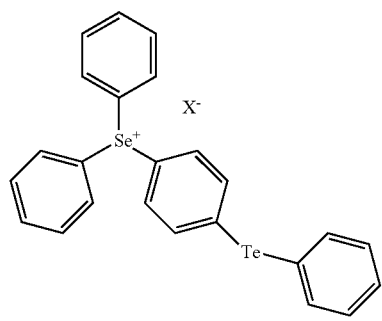
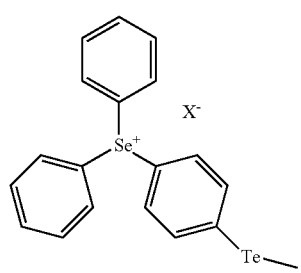
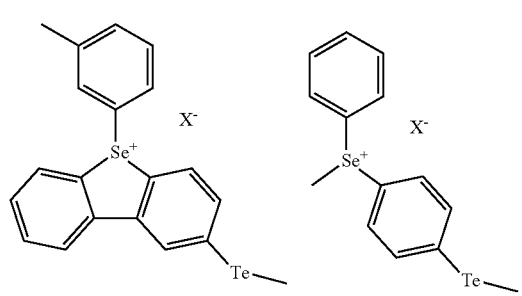
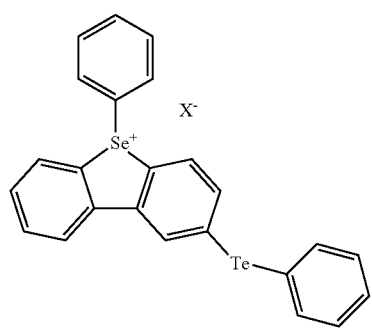
-continued
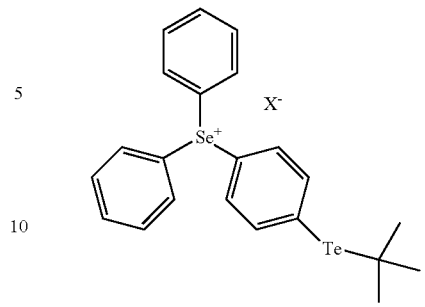
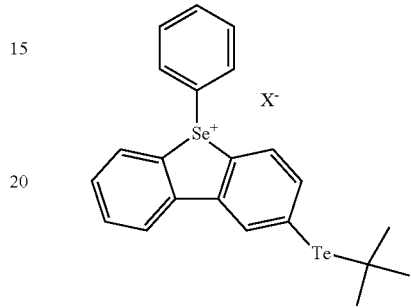
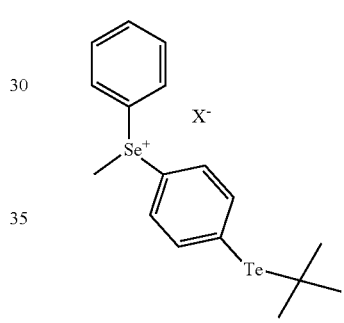
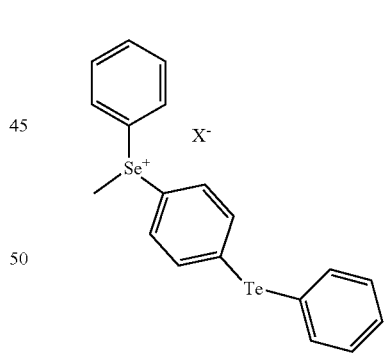
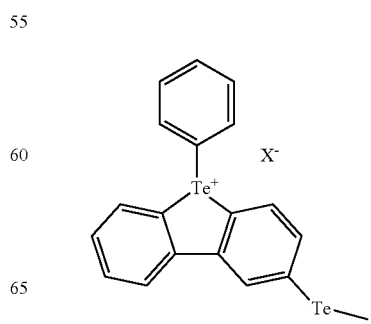

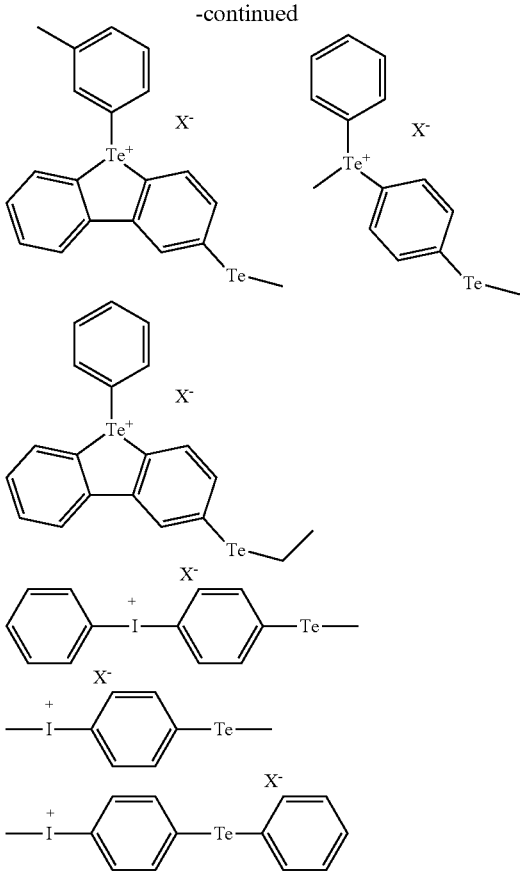

(Photosensitive Compound Including Diazomethane Skeleton)

The photosensitive compound according to some of the embodiments of the present invention can be a photosensitive compound having a diazomethane skeleton including the Te atom containing group. The diazomethane skeleton can include those having a disulfonyl diazomethane skeleton represented by following formula (5), for example. The diazomethane skeleton preferably includes the Te atom containing group directly or via a bonding group.

[Chemical Formula 10]

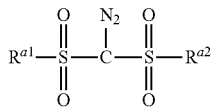
(5)

In formula (5), $R^{a1}$ and $Ra^2$ independently from each other represent either one of a linear, branched, or cyclic hydrocarbon group having 1 to 20 carbons which can be substituted, an aryl group having 5 to 20 carbon atoms which can be substituted, and the like. The hydrocarbon group and the aryl group of $R^{a1}$ and $R^{a2}$ are preferably selected from the same candidates for $R^1$ of formula (1).

At least one of $R^{a1}$ and $R^{a2}$ include one or more divalent Te atom.

The substituent group which can be possessed by $R^{a1}$ and $R^{a2}$ can include; an alkyl group or an alkoxy group having 1 to 4 carbon atoms; an aryl group having 5 to 20 carbon atoms; an aromatic heterocyclic group having 3 to 5 carbon atoms; a nitro group; a halogen atom such as a chlorine atom, a fluorine atom and the like; and the like. Here, the substituent group can be a substituent group similar as the substituent group of $R^1$.

A specific example of $R^{a1}$ and $R^{a2}$ can include an alkyl group such as a methyl group, an ethyl group, a propyl group, an isopropyl group, a n-butyl group, a s-butyl group, a t-butyl group, a pentyl group, a hexyl group, a heptyl group, an octyl group, an amyl group, a cyclopentyl group, a cyclohexyl group, a cycloheptyl group, a norbornyl group, an adamantly group and the like; a phenyl group; an alkoxy phenyl group such as a p-methoxyphenyl group, a m-methoxyphenyl group, an o-methoxyphenyl group, an ethoxyphenyl group, a p-t-butoxyphenyl group, a m-t-butoxyphenyl group and the like; an alkyl phenyl group such as a 2-methylphenyl group, a 3-methylphenyl group, a 4-methylphenyl group, an ethylphenyl group, a 4-t-butylphenyl group, a 4-butylphenyl group, a dimethylphenyl group and the like; an aromatic heterocyclic group; an aralkyl group such as a benzyl group, a phenethyl group and the like; and the like.

In addition, an alkyl group substituted with a halogen atom such as a trifluoromethyl group, a trifluoroethyl group, a trichloroethyl group, a nonafluorobutyl group and the like; an aryl group substituted with a halogen atom such as a fluorophenyl group, a chlorophenyl group, a pentafluorophenyl group and the like; and the like can be preferably mentioned.

(Photosensitive Compound Including Imide Skeleton)

The photosensitive compounds according to some embodiments of the present invention can be a photosensitive compound including an imide skeleton including the Te atom containing group. The imide skeleton can include the ones represented by the following formula (6), and the present invention is not limited so far as the imide skeleton includes the Te atom containing group directly or via a bonding group.

[Chemical Formula 11]

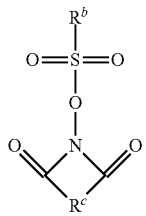
(6)

At least one of $R^b$ and $R^c$ includes one or more divalent Te atom.

$R^b$ represents a linear, branched, or substituted alkyl group having 1 to 8 carbon atoms; an alkenyl group having 2 to 8 carbon atoms; an alkoxyalkyl group having 1 to 8 carbon atoms; an aryl group such as a phenyl group, a naphthyl group or the like; and the like. A part of or all of the hydrogen atoms of these groups can be substituted with a substituent group.

The substituent group which can be possessed by $R^b$ can include an alkyl group or an alkoxy group having 1 to 4 carbon atoms; an aryl group having 5 to 20 carbon atoms; an aromatic heterocyclic group having 3 to 5 carbon atoms; a nitro group; a halogen atom such as a chlorine atom, a fluorine atom and the like; and the like. Here, the substituent group which can be possessed by $R^b$ can be the same substituent group as the substituent group of $R^1$.

In the formula (6), $R^c$ can include the same divalent bonding group as in the photosensitive compound. Preferably, $R^c$ represents an arylene group having 6 to 10 carbon atoms; an alkylene group having 1 to 6 carbon atoms; an alkenylene group having 2 to 6 carbon atoms; and the like. A part of all of the hydrogen atoms of these groups can be substituted with a substituent group.

The substituent group which can be possessed by $R^c$ can include an alkyl group or an alkoxy group having 1 to 4 carbon atoms; an aryl group having 5 to 20 carbon atoms; an aromatic heterocyclic group having 3 to 5 carbon atoms; a nitro group; a halogen atom such as a chlorine atom, a fluorine group and the like; and the like. Here, the substituent group which can be possessed by $R^c$ can be the same substituent group as the substituent group of $R^1$.

Here, as the alkyl group, alkenyl group, and aryl group of $R^b$, the same alkyl group and the aryl group as those of $R^{a1}$ and $R^{a2}$ of formula (5) can also be used.

The alkenyl group of $R^b$ can include a vinyl group, a 1-propenyl group, an allyl group, a 1-butenyl group, 3-butenyl group, an isoprenyl group, a 1-pentenyl group, a 3-pentenyl group, a 4-pentenyl group, a dimethyl allyl group, a 1-hexenyl group, a 3-hexenyl group, a 5-hexenyl group, a 1-heptenyl group, a 3-heptenyl group, a 6-heptenyl group, a 7-octenyl group and the like.

The alkoxy alkyl group of $R^b$ can include a methoxymethyl group, an ethoxymethyl group, a propoxymethyl group, a butoxymethyl group, a pentyloxymethyl group, a hexyloxymethyl group, a heptyloxymethyl group, a methoxyethyl group, an ethoxyethyl group, a propoxyethyl group, a butoxyethyl group, a pentyloxyethyl group, a hexyloxyethyl group, a methoxypropyl group, an ethoxypropyl group, a propoxypropyl group, a butoxypropyl group, a methoxybutyl group, an ethoxybutyl group, a propoxybutyl group, a methoxypentyl group, an ethoxypentyl group, a methoxyhexyl group, a methoxyheptyl group and the like.

The arylene group of $R^c$ can include a 1,2-phenylene group, a 1,8-naphthylene group and the like. The alkylene group of $R^c$ can include a methylene group, an ethylene group, a trimethylene group, a tetramethylene group, a phenylethylene group, a norbornane-2,3-diyl group and the like.

The alkenylene group can include a 1,2-vinylene group, a 1-phenyl-1,2-vinylene group, a 5-norbornene-2,3-diyl group and the like.

A specific imide skeleton can include the followings, however, the imide skeleton is not limited to these.

[Chemical Fomula 12]

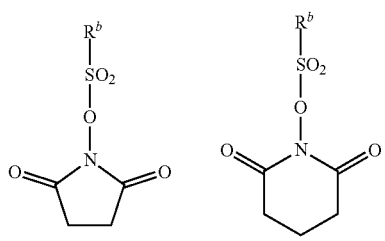

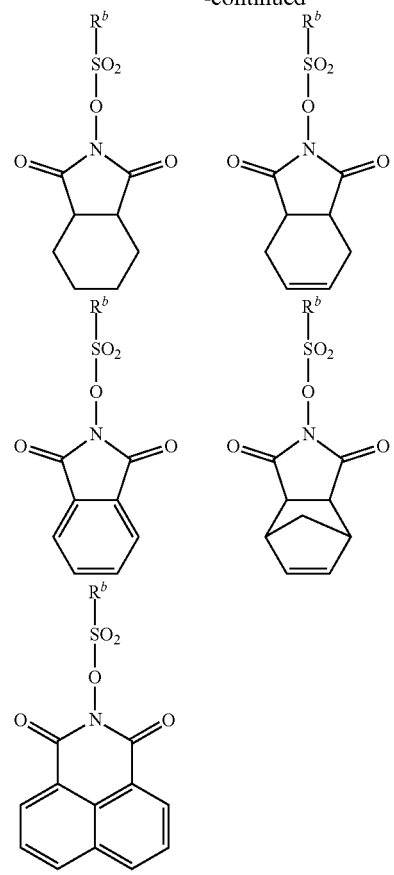

(Photosensitive Compound Including an Oxime Skeleton)

The photosensitive compounds according to some embodiments of the present invention can be a photosensitive compound including an oxime skeleton including the Te atom containing group. The oxime skeleton can include the ones represented by the following formula (7), and the present invention is not limited so far as the oxime skeleton includes the Te atom containing group directly or via a bonding group.

[Chemical Formula 13]

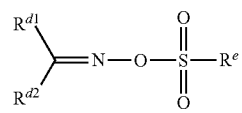

(7)

At least either one of $R^{d1}$, $R^{d2}$, and $R^e$ includes one or more divalent Te atom. At least either one of $R^{d1}$ and $R^{d2}$ preferably includes at least one electron withdrawing group such as a cyano group, a fluorinated alkyl group and the like.

$R^{d1}$ and $R^{d2}$ are, independently from each other, preferably a linear, branched, or cyclic alkyl group having 1 to 20 carbon atoms which can be substituted, an aryl group, a cyano group and the like. A part of or all of the hydrogen atoms of these groups can be substituted with a substituent group. The alkyl group and the aryl group of $R^{d1}$ and $R^{d2}$ can include the alkyl group and the aryl group similar to those of $R^1$ of formula (1).

The substituent group which can be possessed by $R^{d1}$ and $R^{d2}$ can include an alkyl group or an alkoxy group having 1 to 4 carbon atoms; an aryl group having 5 to 20 carbon atoms; an aromatic heterocyclic group having 3 to 5 carbon atoms; a nitro group; a halogen atom such as a chlorine atom, a fluorine atom and the like; and the like. Here, the substituent group can be a substituent group similar to the substituent group of $R^1$.

As $R^e$, the ones similar to $R^b$ of formula (6) can be mentioned. Particularly, $R^e$ represents a linear, branched, or substituted alkyl group; an alkenyl group; an alkoxyalkyl group; an aryl group such as a phenyl group, a naphthyl group or the like; and the like. A part of or all of the hydrogen atoms of these groups can be substituted with a substituent group.

The substituent group which can be possessed by $R^e$ can include; an alkyl group or an alkoxy group having 1 to 4 carbon atoms; an aryl group having 5 to 20 carbon atoms; an aromatic heterocyclic group having 3 to 5 carbon atoms; a nitro group; a halogen atom such as a chlorine atom, a fluorine atom and the like; and the like. Here, the substituent group can be a substituent group similar to the substituent group of $R^1$.

As the alkyl group of $R^e$, number of carbon atoms of the alkyl group is preferably 1 to 20, more preferably 1 to 10, further preferably 1 to 8, especially preferably 1 to 6, and most preferably 1 to 4. As the alkyl group, an alkyl group being partially or fully halogenated is especially preferable (hereinafter can be referred to as halogenated alkyl group). Here, the partially halogenated alkyl group means an alkyl group having a part of hydrogen atoms substituted with halogen atoms. The fully halogenated alkyl group means an alkyl group having all of the hydrogen atoms substituted with halogen atoms. The halogen atom can include a fluorine atom, a chlorine atom, a bromine atom, an iodine atom and the like, and the fluorine atom is especially preferable. That is, halogenated alkyl group is preferably a fluorinated alkyl group.

Regarding the aryl group, number of carbon atoms of the aryl group is preferably 4 to 20, more preferably 4 to 10, and most preferably 6 to 10. As the aryl group, an aryl group being partially or fully halogenated is especially preferable. Here, the partially halogenated aryl group means an aryl group having a part of hydrogen atoms substituted with halogen atoms. The fully halogenated aryl group means an aryl group having all of the hydrogen atoms substituted with halogen atoms.

$R^{d1}$ and $R^{d2}$ can bond with each other to form a ring.
(Photosensitive Compound Including Other Skeleton)

The photosensitive compound according to some embodiments of the present invention is not particularly limited so long as they include a Te atom containing group. In addition to the ones mentioned above, the photosensitive compound can be an onium salt such as a phosphonium salt, an ammonium salt, a pyridinium salt and the like; a glyoxime compound; a sulfone compound such as a bis-sulfonic acid compound, a β-keto sulfonic acid compound, a di-sulfonic acid compound and the like; a sulfonic acid ester and the like. The photosensitive compound according to some embodiments of the present invention can be used alone or two or more can be used in combination as a component of the resist composition.
(Embodiment of Photosensitive Compound)

The photosensitive compound according to some embodiments of the present invention is suitably used as a photoacid generator, a photodegradable base, a sensitizer and the like. It is especially preferable that the photosensitive compound according to some embodiments of the present invention is used as a photoacid generator and a photodegradable base.

In addition, as discussed, the photosensitive compounds according to some embodiments of the present invention can be a polymer. When the photosensitive compound is a polymer, the polymer can be a homopolymer when it includes a unit which can function as a photosensitive compound, and can also be a copolymer including another unit. The another unit when the polymer is a copolymer can include a unit which can react as an acid-reactive compound, a hydroxyaryl group-including unit and the like. The unit which can react as an acid-reactive compound, the hydroxyaryl group-including unit and the like will be described hereinafter.
<2> Synthetic Method of Photosensitive Compound The photosensitive compound according to some embodiments of the present invention can be synthesized by the following method.

In the following, a synthesis example of a sulfonium salt where Y in formula (2) is a sulfur atom is shown. First, magnesium is added to a THF, followed by heating to 40 to 50° C. To this solution, a tetrahydrofuran (THF) solution of a sulfide compound including —$R^{2a}$ group and —$R^{2b}$—Br group is added in a dropwise manner. Further, a THF solution of an organic tellurium compound including $R^1$ group is added in a dropwise manner at 50° C. or lower. Grignard reaction is carried out for 1 to 3 hours, thereby obtaining a tellurium containing sulfide.

The tellurium containing sulfide is oxidized into a sulfoxide using MCPBA and the like, followed by Grignard reaction to obtain a tellurium containing sulfonium chloride salt. Then, tellurium containing sulfonium salt compound including a corresponding $X^-$ is obtained by salt exchange and the like.

[Chemical Formula 14]

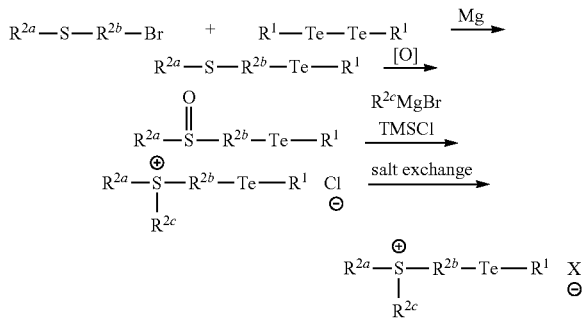

Otherwise, the tellurium containing sulfide is allowed to react with a methyl sulfate iodonium including -$R^{2c}$ group, thereby obtaining a tellurium containing sulfonium methyl sulfate. Subsequently, salt exchange and the like are carried out to obtain the tellurium containing sulfonium salt compound including corresponding $X^-$.

$R^{2a}$ and $R^{2c}$ are selected from the same candidates as $R^1$. $R^{2b}$ is selected from the same candidates as $R^3$.

When Y is an iodine atom, synthesis can be carried out in the following manner.

First, 1-bromo-4-iodobenzene, trifluoromethanesulfonic acid, benzene, and dichloromethane are mixed. Subsequently, a dichloromethane solution of MCPBA is added in a dropwise manner to this mixture, and reaction is allowed to proceed, thereby obtaining 4-bromophenyl phenyl-iodoniumtrifluoromethanesulfonate. Then, to a THF solution of magnesium, a THF solution of 4-bromophenyl phenyl-iodoniumtrifluoromethanesulfonate is added in a dropwise manner. To this mixture, a THF solution of an organic tellurium compound including $R^1$ group is added in a dropwise manner, and then Grignard reaction is allowed to proceed, thereby obtaining a tellurium containing iodonium. Subsequently, salt exchange and the like is carried out to obtain a tellurium containing iodonium salt compound including corresponding $X^-$.

<3> Resist Composition

One embodiment of the present invention relates to a resist composition including the photosensitive compound. Regarding the resist composition, the photosensitive compound can be used as one or more of photoacid generator, photodegradable base and sensitizer.

When one of the photosensitive compound according to the present invention is used as the photoacid generator and as the photodegradable base, and the photosensitive compound has an onium structure, the anion of the photodegradable base is preferably used in combination with an arbitrary anion having a weaker acid strength than the anion of the photoacid generator. More particularly, it is preferable that pKa of the photoacid generator is −3 or lower. Such anion can include a fluorine substituted sulfonic acid and the like.

In some of the embodiments of the present invention, pKa is a value obtained by analysis using ACD labs (manufactured by FUJITSU LIMITED).

The resist composition can further include a photoacid generator and a photodegradable base in addition to the photosensitive compound of some of the embodiments of the present invention.

Further preferably, the resist composition further includes an acid-reactive compound.

Hereinafter, each of the components included in the resist composition is explained.

(Other Photoacid Generator)

When the resist composition of some of the embodiments of the present invention uses the photosensitive compound of some of the embodiments of the present invention as a photoacid generator, other photoacid generator (hereinafter referred to as "second photoacid generator") can be included. Such second photoacid generator can include there is no particular limitation so long as it can be used for an ordinary resist composition, and an onium salt compound such as a sulfonium salt, an iodonium salt and the like, a N-sulfonyloxyimide compound, an oxime sulfonate compound, an organic halogen compound, a sulfonyl diazomethane compound and the like for example. These second photoacid generator can be used alone or two or more can be used in combination.

As the sulfonium salt, those disclosed in publication No. WO 2011/093139 can be mentioned.

The second photoacid generator can be included in the resist composition as a low molecular component, or can be included as a unit of a polymer. That is, the second photoacid generator can be included in the polymer as a unit, by bonding an arbitrary position of the photoacid generator to the polymer main chain. For example, when the photoacid generator is a sulfonium salt, it is preferable that the photoacid generator includes a bonding group which bonds with the polymer main chain directly or via a bonding group, in place of one H included in the sulfonium salt.

The total content of the photoacid generator (including the second photoacid generator) in the resist composition of one of the embodiments of the present invention is preferably 1 to 50 parts by mass in total with respect to 100 parts by mass of an acid-reactive compound explained hereinafter, more preferably 3 to 30 parts by mass, and further preferably 5 to 25 parts by mass.

When the photoacid generator bonds with the polymer, the total content of the photoacid generator is based on a mass excluding the polymer main chain.

(Other Photodegradable Base)

The resist composition of one of the embodiments of the present invention can include other photodegradable base. As the photodegradable base, those similar as the cations possessed by the other photoacid generator can be used. In such cases, the anion of the photodegradable base is preferably an anion having a weaker acid strength than the anion of the photoacid generator.

The content of the photodegradable base in the resist composition is preferably 0.5 to 50 parts by mass with respect to 100 parts by mass of an acid-reactive compound explained hereinafter, more preferably 1 to 30 parts by mass, and further preferably 2 to 25 parts by mass.

The content of the photodegradable base in the resist composition is preferably 1 to 50 parts by mass with respect to 10 parts by mass of the photoacid generator, more preferably 3 to 25 parts by mass. By allowing the photodegradable base to be contained in the resist composition within the afore-mentioned range, superior characteristics such as sensitivity, resolution, and pattern forming ability can be achieved.

In the calculation of the content, organic solvent is not included as the component of the resist composition.

When the photodegradable base bonds with the polymer, the total content of the photoacid generator is based on a mass excluding the polymer main chain.

Here, the photodegradable base can be used alone or two or more of photodegradable bases can be used in combination.

(Acid-reactive Compound)

The resist composition of some of the embodiments of the present invention preferably includes an acid-reactive compound.

The acid-reactive compound preferably includes a protecting group which is deprotected by acid, polymerizes by acid, or cross-links by acid. That is, the acid-reactive compound preferably is at least either one of a compound selected from the group consisting of a compound including a protecting group which is deprotected by acid, a compound including a polymerizing group which polymerize by acid, and a cross-linking agent which cross-links by acid.

The compound including a protecting group which is deprotected by acid is a compound which is deprotected by acid to generate a polar group, thereby causing change in the solubility with respect to a developer. For example, when an aqueous development using an alkali developer and the like is carried out, the compound including the protecting group which is deprotected by acid is insoluble with respect to the alkali developer. However, when an acid is generated from the photoacid generator by exposure, the acid deprotects the protecting group from the compound at the exposure portion, thereby allowing the compound to be soluble with respect to the alkali developer.

In some embodiments of the present invention, the developer is not limited to the alkali developer, and can be a neutral developer or an organic solvent developer. Accordingly, when the organic solvent developer is used, the compound including a protecting group which is deprotected by acid is a compound of which protecting group is deprotected from the compound by the acid generated by the photoacid generator at the exposure portion, thereby generating a polar group, resulting in decrease in the solubility with respect to the organic solvent developer.

The polar group can include a hydroxy group, a carboxy group, an amino group, a sulfo group and the like.

A specific example of the protecting group which is deprotected by acid can include an ester group, an acetal group, a tetrahydropyranyl group, a carbonate group, a siloxy group, a benzyloxy group and the like. As a compound including such protecting group, a compound including a styrene skeleton having these protecting groups as pendant groups, a compound including a methacrylate or an acrylate skeleton and the like can be suitably used.

The compound including the protecting group which is deprotected by acid can be a low molecular compound including a protecting group and can be a polymer including a protecting group. In some of the embodiments of the present invention, a low molecular compound is a compound having a weight average molecular weight of lower than 2000, and the polymer is a compound having a weight average molecular weight of 2000 or more.

The compound including a polymerizing group which polymerize by acid is a compound which can change a solubility of a compound with respect to the developer due to polymerization by acid. For example, when an aqueous developer is used, the compound including a polymerizing group reacts with a compound which is soluble with respect to the aqueous developer, and then solubility of the compound with respect to the aqueous developer becomes lower, after polymerization. Specifically, a compound including an epoxy group, a vinyloxy group, an oxetanyl group and the like can be mentioned.

The compound including a polymerizing group which polymerize by acid can be a polymerizable low molecular compound and can be a polymerizable polymer.

The cross-linking agent which cross-links by acid is a compound which can change a solubility of a compound with respect to the developer due to cross-linking by acid. For example, when an aqueous developer is used, the cross-linking agent reacts with a compound which is soluble with respect to the aqueous developer, and lowers the solubility of the compound with respect to the aqueous developer, after polymerization or cross-linking. Specifically, a cross-linking agent including an epoxy group, a vinyloxy group, a 1-alkoxyamino group, an oxetanyl group and the like can be mentioned. When the compound is the cross-linking agent having cross-linking ability, as the object compound to which the cross-linking agent cross-links, that is, the compound of which solubility with respect to the developer changes by reacting with the cross-linking agent can include a compound including a phenolic hydroxyl group and the like.

The compound which cross-links by acid can be a polymerizable low molecular compound and can be a polymerizable polymer.

When the acid-reactive compound is a polymer, other unit which is usually used in the resist composition can be included in the polymer in addition to the unit bonded with the reactive compound. Such other unit can include, for example, a unit (I) including at least either one of a skeleton selected from the group selected from a lactone skeleton, a sulton skeleton, a lactam skeleton and the like; a unit (II) including at least either one of a substituent group selected from a group consisting of a substituent group including an ether bond, an ester bond, and an acetal structure, a hydroxy group and the like; a hydroxyaryl group including unit (III); and the like. Further, the other unit can include a unit (IV) having bonded thereto the photodegradable base, and a unit (V) having bonded thereto the photoacid generator.

In some embodiments of the present invention, ratio of each unit of the polymer is not particularly limited. Here, when the unit bonded with the acid-reactive compound is included as the unit in the same polymer with the other unit, the unit bonded with the acid-reactive compound is preferably contained by 10 to 70 mol % with respect to the entire unit of the polymer, more preferably 15 to 65 mol %, and further preferably 20 to 60 mol %.

The unit (I) is preferably contained by 0 to 60 mol % with respect to the entirety, more preferably 10 to 60 mol %, and further preferably 20 to 60 mol %. The unit (II) is preferably contained by 0 to 70 mol %, more preferably 5 to 70 mol %, and further preferably 10 to 60 mol %. The unit (III) is preferably contained by 0 to 90 mol % with respect to the entirety, and more preferably 10 to 80 mol %. The unit (IV) is preferably contained by 0 to 30 mol %, more preferably 1 to 30 mol %, and further preferably 3 to 20 mol %. The unit (V) is preferably contained by 0 to 30 mol %, more preferably 1 to 30 mol %, and further preferably 3 to 20 mol %.

The polymer can be synthesized in the following manner, for example. Monomer which structure each of the units is polymerized by known radical polymerization and the like, using a radical polymerization initiator such as azobisisobutyronitrile (AIBN), dimethyl azobisisobutyrate and the like thereby obtaining the polymer.

Here, when polymerization is carried out, a chain transfer agent such as $HS-CH_2-CH_2-CH_2-C(CF_3)_2-OH$ and the like can be used in combination, thereby introducing $-C(CF_3)_2-OH$ group at the terminal of the polymer. As discussed, the polymer including a hydroxyalkyl group having a part of the hydrogen atom of the alkyl group substituted with fluorine atom is effective to reduce development defect and to reduce LER.

(Other Components)

The resist composition of one of the embodiments of the present invention can include in combination an organic solvent, an acid diffusion control agent, a surfactant, an organic carboxylic acid, a dissolution inhibitor, a stabilizer, a colorant, a sensitizer and the like that are used in ordinary resist composition, as an arbitrary component in addition to the afore-mentioned component if necessary.

As the organic solvent, for example, ethylene glycol monoethyl ether acetate, cyclohexanone, 2-heptane, propyleneglycol monomethylether (PGME), propyleneglycol monomethylether acetate (PGMEA), propyleneglycol monomethylether propionate, propyleneglycol monoethylether acetate, methyl 3-methoxypropionate, ethyl 3-ethoxypropionate, methyl β-methoxyisobutyrate, ethylbutyrate, propylbutyrate, methyl isobutyl ketone, ethyl acetate, isoamyl acetate, ethyl lactate, toluene, xylene, cyclohexyl acetate, diacetone alcohol, N-methyl pyrrolidone, N,N-dimethylforamide, γ-butyrolactone, N—N-dimethylacetamide, propylene carbonate, ethylene carbonate and the like are preferable. These organic solvents can be used alone or in combination.

The acid diffusion control agent controls the diffusion of the acid generated from the photoacid generator into the resist film, thereby achieving an effect to control an unfavorable chemical reaction in the non-disposed region. Accordingly, the shelf stability of the resist composition thus obtained can be further improved, resolution as the resist can be further improved, change in line-width of the resist pattern due to alteration in the time elapsed from exposure to developing process can be suppressed, and a resist composition having superior processing stability can be obtained.

The acid diffusion control agent can include, for example, a compound including one nitrogen atom in the same molecule, a compound including two nitrogen atoms, a compound including three nitrogen atoms, a compound including an amide group, an urea compound, a nitrogen containing heterocyclic compound and the like. As the acid diffusion control agent, the photodegradable base other than the metal-including onium salt compound of one of the embodiments of the present invention which is sensitized by exposure and generates a weak acid can be used. Specifically, the compounds disclosed in Japanese Patent Publication JP 3577743, Japanese Patent Application Publications JP 2001-215689, JP 2001-166476, JP 2008-102383, JP 2010-243773, JP2011-37835, and JP 2012-173505 can be mentioned.

When the acid diffusion control agent is contained, the content thereof is preferably 0.01 to 20 parts by mass with respect to 100 parts by mass of the acid-reactive compound, more preferably 0.03 to 15 parts by mass, and further preferably 0.05 to 10 parts by mass. In the content, the photodegradable base is not included.

The surfactant is preferably used to improve coatability. An example of the surfactant can include nonion surfactants such as polyoxyethylene alkylethers, polyoxyethylene alkylallylethers, polyoxyethylene polyoxypropylene block copolymers, sorbitan fatty acid esters, polyoxyethylene sorbitan fatty acid esters and the like, fluorine-based surfactants, organosiloxane polymer and the like.

The content of the surfactant is preferably 0.0001 to 2 parts by mass with respect to 100 parts by mass of the acid-reactive compounds, and more preferably 0.0005 to 1 part by mass.

The organic carboxylic acid can include an aliphatic carboxylic acid, an alicyclic carboxylic acid, an unsaturated aliphatic carboxylic acid, an oxycarboxylic acid, an alkoxycarboxylic acid, a ketocarboxylic acid, a benzoic acid derivative, a phthalic acid, a terephthalic acid, an isophthalic acid, a 2-naphthoic acid, a 1-hydroxy-2-naphthoic acid, a 2-hydroxy-3-naphthoic acid and the like. When electron beam exposure is carried out under vacuum, there is a possibility that the organic carboxylic acid would volatize from the surface of the resist film and contaminate the inside of the drawing chamber. Therefore, preferable organic carboxylic acid is the aromatic organic carboxylic acid. Among the aromatic organic carboxylic acid, benzoic acid, 1-hydroxy-2-naphtoic acid and 2-hydroxy-3-naphthoic acid are preferable for example.

The content of the organic carboxylic acid is preferably 0.01 to 10 parts by mass with respect to 100 parts by mass of the acid-reactive compound, more preferably 0.01 to 5 parts by mass, and further preferably 0.01 to 3 parts by mass.

The resist composition component dissolves in the organic solvent, and the amount of dissolution is preferably 1 to 40 mass % as solid concentration, more preferably 1 to 30 mass %, and further preferably 3 to 20 mass %.

When the resist composition of one of the embodiments of the present invention includes a polymer, the polymer preferably has a weight average molecular weight of 2000 to 200000, more preferably 2000 to 50000, and further preferably 2000 to 15000. The degree of distribution (molecular weight distribution) (Mw/Mn) is 1.0 to 2.2 in terms of sensitivity, and more preferably 1.2 to 2.0.

In some of the embodiments of the present invention, the weight average molecular weight and the molecular weight distribution of the polymer is defined as the polystyrene equivalent value obtained by GPC measurement.

The resist composition of one of the embodiments of the present invention can include a fluorine-containing water repellent polymer.

The water repellent polymer can include, with no particular limitation, those usually used in the immersion exposure process. Here, it is preferable that the water repellent polymer has a larger fluorine content rate than the polymer. As such, when a resist film is formed using the resist composition, the fluorine-containing water repellent polymer can be distributed unevenly on the surface of the resist film due to the water repellent property of the fluorine-containing water repellent polymer.

Regarding the fluorine content rate of the fluorine-containing water repellent polymer, it is preferable that hydrogen atom of the hydrocarbon group in the fluorine-containing water repellent polymer is fluorinated by 25% or more, and is more preferably fluorinated by 50% or more.

Regarding the amount of the fluorine-containing water repellent polymer contained in the resist composition, it is preferable that the fluorine-containing water repellent polymer is contained by 0.5 to 10 mass % with respect to 100 parts by mass of the polymer (polymer other than the fluorine-containing water repellent polymer) of one of the embodiments of the present invention, in terms of improvement in the hydrophobicity of the resist film. The fluorine-containing water repellent polymer can be used alone, or two or more of the fluorine-containing water repellent polymer can be used in combination.

The composition of one of the embodiments of the present invention can be obtained by mixing each of the components of the composition, and the method of mixing is not particularly limited.

<4> Method of Manufacturing Device

One of the embodiments of the present invention is a method of manufacturing a device comprising the steps of a resist film forming step to form a resist form a resist film by applying the resist composition on a substrate, an exposure step to expose the resist film, and a resist pattern forming step to form a resist pattern by developing the exposed resist film.

One of the embodiments of the present invention can be a method of manufacturing a substrate having a pattern before obtaining a divided chip, comprising the steps of a resist film forming step to form a resist film by using the resist composition, and a pattern forming step to form a pattern.

The active energy ray used for exposure in the exposure step means KrF excimer laser, ArF excimer laser, $F_2$ excimer laser, UV such as i line and the like, visible ray, X-ray, electron beam, ion beam, EUV and the like, so long as a ray or a particle beam which can activate the photosensitive compound of one of the embodiments of the present invention to generate acid.

In one of the embodiments of the present invention, electron beam (EB), extreme ultraviolet (EUV) and the like can be preferably mentioned as the active energy ray used for exposure in the exposure step.

The exposure dose of the ray would differ by the type and formulation ratio of each of the components in the photocurable composition, the film thickness of the film and the like. Here, the exposure dose of the ray is preferably 1 J/cm$^2$ or lower or 1000 μC/cm$^2$ or lower.

When the resist composition includes the sensitizer or includes a corresponding sensitizer in the polymer as a sensitizing unit, it is preferable to perform a second exposure by UV and the like after a first exposure performed by the electron beam, EUV or the like.

EXAMPLES

Hereinafter, some of the embodiments of the present invention will be explained with reference to Examples, however, the present invention shall not be limited to these Examples.

<Synthesis of Tellurium Containing Sulfonium Salt 1>

Synthesis Example 1

Synthesis of Tellurium Containing Sulfide

A reactor vessel containing magnesium (0.64 g) and THF is heated to 40 to 50° C., followed by dropwise addition of a THF solution of 2-bromo dibenzothiophene (5.79 g), thereby preparing a Grignard reagent. Subsequently, a THF solution of diphenyl ditelluride (8.19 g) is added in a dropwise manner, and general after-treatment is performed after 1 to 3 hours of reaction. Purification is performed by silica gel column chromatography (n-hexane 100%) to obtain the tellurium containing sulfide (3.14 g).

[Chemical Formula 15]

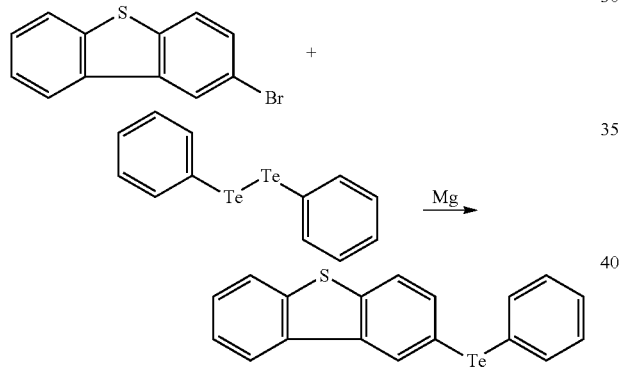

Synthesis Example 2

Synthesis of Tellurium Containing Sulfoxide

The tellurium containing sulfide obtained in Synthesis Example 1 (1.16 g), MCPBA (0.76 g), and dichloromethane (5.78 g) are mixed and allowed to react at 25° C. for 1 to 3 hours. General after-treatment is performed, and then purification is performed by silica gel column chromatography (methanol/dichloromethane=20/80) to obtain the tellurium containing sulfoxide (0.60 g).

[Chemical Formula 16]

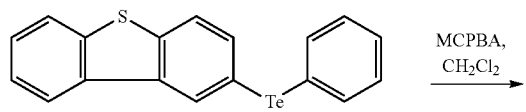

Synthesis Example 3

Synthesis of Tellurium Containing Sulfonium Chloride Salt

The tellurium containing sulfoxide obtained in Synthesis Example 2 (2.00 g), THF solution of 1M phenyl magnesium bromide (6.00 g), trimethyl chlorosilane (1.60 g), and THF (36.0 g) are mixed and agitation is performed for 1 hour. General after-treatment is performed, and then purification is performed by silica gel column chromatography (methanol/dichloromethane=10/90) to obtain the tellurium containing sulfonium chloride salt (0.06 g).

[Chemical Formula 7]

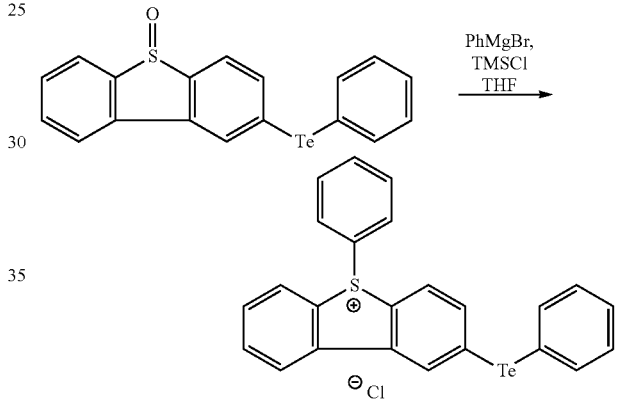

Synthesis Example 4

Synthesis of Tellurium Containing Sulfonium Salt 1

The tellurium containing sulfonium chloride salt obtained in Synthesis Example 3 (1.62 g), potassium nonafluorobutanesulfonate (1.21 g), dichloromethane (16.2 g), and water (16.2 g) are mixed and agitation is performed for 1 hour. After washing with water, purification is performed by silica gel column chromatography (methanol/dichloromethane=5/95) to obtain the tellurium containing sulfonium salt 1 (1.9 g).

[Chemical Formula 18]

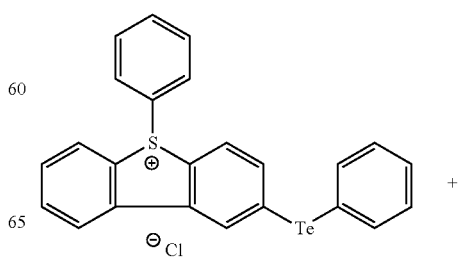

-continued

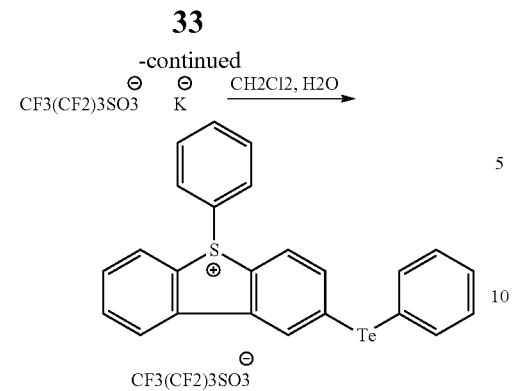

(tellurium containing sulfonium salt 1)

<Synthesis of Tellurium Containing Sulfonium Salt 2>

Synthesis Example 5

Synthesis of Tellurium Containing Sulfonium Salt 2

Similar procedure is carried out as Synthesis Example 4 except for using sodium 4-(1-adamantane carbonyloxy) 1,1, 2-trifluorobutane-1-sulfonate in place of potassium nonafluorobutanesulfonate.

[Chemical Formula 19]

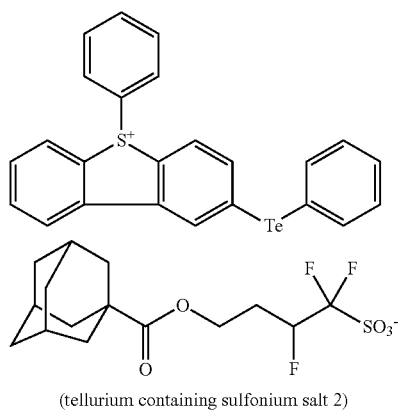

(tellurium containing sulfonium salt 2)

<Synthesis of Tellurium Containing Sulfonium Salt 3>

Synthesis Example 6

Synthesis of Tellurium Containing Sulfonium Salt 3

Similar procedure is carried out as Synthesis Example 4 except for using sodium 4-(3-hydroxy-1-adamantane carbonyloxy) 1,1,2-trifluorobutane-1-sulfonate in place of potassium nonafluorobutanesulfonate.

[Chemical Formula 20]

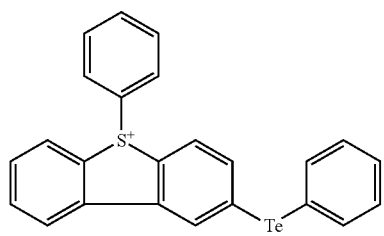

-continued

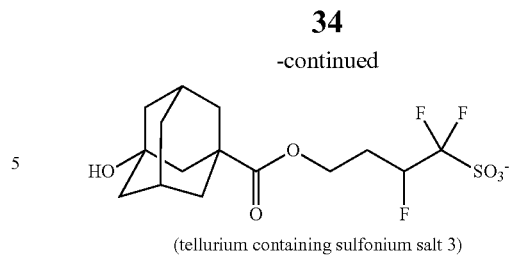

(tellurium containing sulfonium salt 3)

<Synthesis of Tellurium Containing Sulfonium Salt 4>

Synthesis Example 7

Synthesis of Tellurium Containing Sulfonium Salt 4

Similar procedure is carried out as Synthesis Examples 1 to 4 except for using 4-bromophenyl phenylsulfide in place of 2-boromobenzothiophene in Synthesis Example 1 and for using sodium 4-(3-hydroxy-1-adamantane carbonyloxy) 1,1,2-trifluorobutane-1-sulfonate in place of potassium nonafluorobutanesulfonate in Synthesis Example 4.

[Chemical Formula 21]

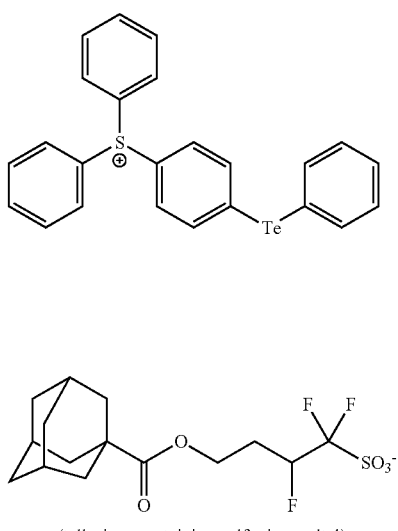

(tellurium containing sulfonium salt 4)

<Synthesis of Polymer (A-1)>

Synthesis Example 8

Synthesis of Polymer (A-1)

Monomers which constitute each of the constituting unit are polymerized by known radical polymerization and the like using azobisisobutyronitrile (AIBN) as the radical initiator, thereby obtaining polymer A-1 shown below (weight average molecular weight: approximately 10000). In the following formula, relations of a=0.4, b=0.4, and c=0.2 are satisfied, however, the monomer ratio of the unit in the polymer of some embodiments of the present invention is not limited to the followings.

[Chemical Formula 22]

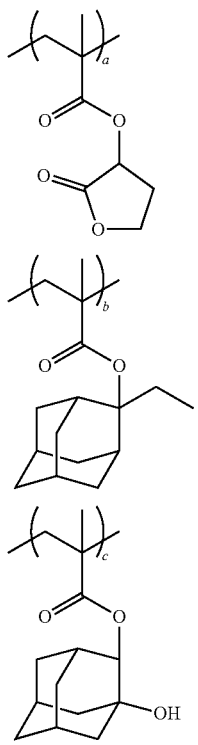

<Synthesis of Polymer (A-2)>

Synthesis Example 9

Synthesis of Polymer (A-2)

Monomers which constitute each of the constituting unit are polymerized by known radical polymerization and the like using azobisisobutyronitrile (AIBN) as the radical initiator, thereby obtaining polymer A-2 shown below (weight average molecular weight: approximately 10000). In the following formula, relations of a=0.4, b=0.4, and c=0.2 are satisfied, however, the monomer ratio of the unit in the polymer of some embodiments of the present invention is not limited to the followings.

[Chemical Formula 23]

(A-2)

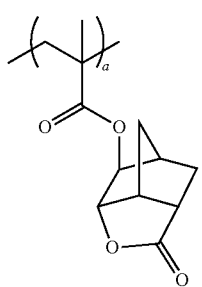

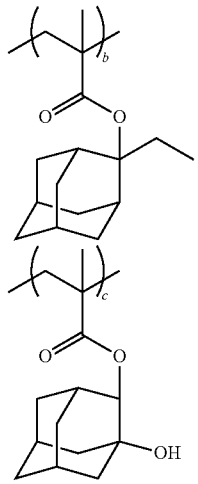

(A-1)

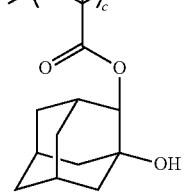

<Synthesis of Polymer (A-3)>

Synthesis Example 10

Synthesis of Polymer (A-3)

Monomers which constitute each of the constituting unit are polymerized by known radical polymerization and the like using azobisisobutyronitrile (AIBN) as the radical initiator, thereby obtaining polymer A-3 shown below (weight average molecular weight: approximately 10000). In the following formula, relations of a=0.4, b=0.4, and c=0.2 are satisfied, however, the monomer ratio of the unit in the polymer of some embodiments of the present invention is not limited to the followings.

[Chemical Formula 24]

(A-3)

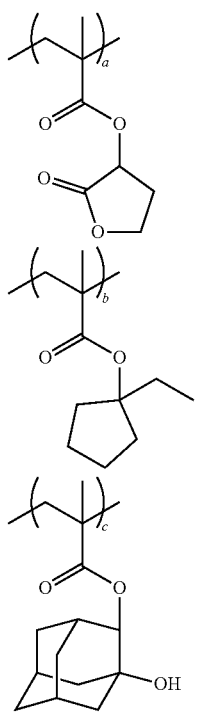

Example 1

<Preparation of Resist Composition>

Either one of polymer (A-1), polymer (A-2), and polymer (A-3) as the base polymer (100 parts by mass), tellurium containing sulfonium salt 1 as the photoacid generator (8 parts by mass), and propylene glycol monomethyl ether acetate as the solvent (1800 parts by mass) are mixed, followed by filtration using a PTFE filter, thereby preparing a resist composition (H-1). Details of the resist composition are shown in Table 1.

Examples 2 to 12

Either one of the tellurium containing sulfonium salts 2 to 4 synthesized as above are used by the formulation amount shown in Table 1 in place of the tellurium containing sulfonium salt 1 as the photoacid generator, and the rest of the conditions are carried out in a similar manner as Example 1 to obtain the resist compositions (H-2) to (H-12).

Comparative Examples 1 to 12

Either one of the photoacid generators (B-1) to (B-4) are used by the formulation amount shown in Table 1 in place of the tellurium containing sulfonium salt 1 as the photoacid generator, and the rest of the conditions are carried out in a similar manner as Example 1 to obtain the resist compositions (H-13) to (H-24).

Here, the photoacid generators (B-1) to (B-4) are shown below.

[Chemical Formula 25]

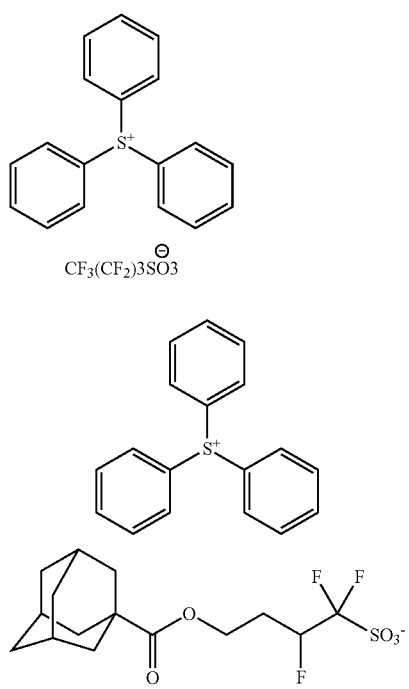

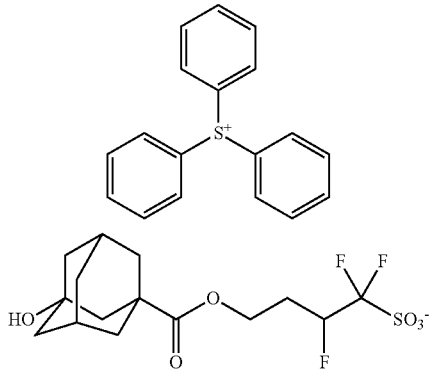

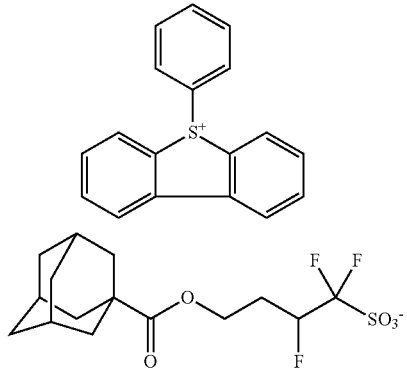

TABLE 1

| resist composition | polymer type | polymer formulation amount (parts by mass) | photoacid generator type | photoacid generator formulation amount (parts by mass) | solvent formulation amount (parts by mass) |
|---|---|---|---|---|---|
| Ex. 1  | H-1  | A-1 | 100 | Te containing sulfonium salt 1 | 8.0 | 1800 |
| Ex. 2  | H-2  | A-1 | 100 | Te containing sulfonium salt 2 | 8.7 | 1800 |
| Ex. 3  | H-3  | A-1 | 100 | Te containing sulfonium salt 3 | 8.9 | 1800 |
| Ex. 4  | H-4  | A-1 | 100 | Te containing sulfonium salt 4 | 8.7 | 1800 |
| Ex. 5  | H-5  | A-2 | 100 | Te containing sulfonium salt 1 | 8.0 | 1800 |
| Ex. 6  | H-6  | A-2 | 100 | Te containing sulfonium salt 2 | 8.7 | 1800 |
| Ex. 7  | H-7  | A-2 | 100 | Te containing sulfonium salt 3 | 8.9 | 1800 |
| Ex. 8  | H-8  | A-2 | 100 | Te containing sulfonium salt 4 | 8.7 | 1800 |
| Ex. 9  | H-9  | A-3 | 100 | Te containing sulfonium salt 1 | 8.0 | 1800 |
| Ex. 10 | H-10 | A-3 | 100 | Te containing sulfonium salt 2 | 8.7 | 1800 |

TABLE 1-continued

| resist composition | polymer type | polymer formulation amount (parts by mass) | photoacid generator type | photoacid generator formulation amount (parts by mass) | solvent formulation amount (parts by mass) |
|---|---|---|---|---|---|
| Ex. 11 | H-11 | A-3 | 100 | Te containing sulfonium salt 3 | 8.9 | 1800 |
| Ex. 12 | H-12 | A-3 | 100 | Te containing sulfonium salt 4 | 8.7 | 1800 |
| Comp. Ex. 1 | H-13 | A-1 | 100 | B-1 | 5.9 | 1800 |
| Comp. Ex. 2 | H-14 | A-1 | 100 | B-2 | 6.6 | 1800 |
| Comp. Ex. 3 | H-15 | A-1 | 100 | B-3 | 6.8 | 1800 |
| Comp. Ex. 4 | H-16 | A-1 | 100 | B-4 | 6.6 | 1800 |
| Comp. Ex. 5 | H-17 | A-2 | 100 | B-1 | 5.9 | 1800 |
| Comp. Ex. 6 | H-18 | A-2 | 100 | B-2 | 6.6 | 1800 |
| Comp. Ex. 7 | H-19 | A-2 | 100 | B-3 | 6.8 | 1800 |
| Comp. Ex. 8 | H-20 | A-2 | 100 | B-4 | 6.6 | 1800 |
| Comp. Ex. 9 | H-21 | A-3 | 100 | B-1 | 5.9 | 1800 |
| Comp. Ex. 10 | H-22 | A-3 | 100 | B-2 | 6.6 | 1800 |
| Comp. Ex. 11 | H-23 | A-3 | 100 | B-3 | 6.8 | 1800 |
| Comp. Ex. 12 | H-24 | A-3 | 100 | B-4 | 6.6 | 1800 |

<Evaluation>

Each of the resist composition is spin coated on a silicon wafer using a spin coater, followed by pre-baking for 60 seconds at 110° C. on a hot plate, thereby obtaining a coating film having a film thickness of 150 nm. A mask is used so that a line pattern of 90 nm can be obtained, and the coating film is exposed by an ArF excimer laser, followed by post-baking for 90 seconds at 110° C. Then, developing is carried out for 60 seconds using a 2.38 mass % aqueous tetramethyl ammonium hydroxide, followed by rinsing with purified water for 30 seconds, thereby obtaining a pattern-formed substrate.

Resolution, depth of focus, and line edge roughness of Comparative Example 1 is taken as the standard, and sensitivity, resolution, depth of focus and line edge roughness of Examples 1 to 12 and Comparative Examples 2 to 12 are evaluated by the following criteria. Here, scanning electron microscope is used for the measurement of the resist pattern.

Excellent: improvement by 10% or more compared with Comparative Example 1 observed
Good: improvement by 5% or more and less than 10% compared with Comparative Example 1 observed
Poor: improvement by less than 5% compared with Comparative Example 1 observed (Resolution)

Resolution shows a width of line pattern (nm) which can be resolved by the minimum exposure amount to reproduce a line pattern of 90 nm. That is, resolution shows a marginal resolving ability. Regarding resolution, the smaller the value, the better resolution.

(Depth of Focus)

The position of focus is moved up and down, and exposure is performed by minimum exposure amount to reproduce a line pattern of 90 nm, followed by post baking (PEB) and development. The depth of focus shows the range of focus which allows to reproduce the line pattern of 90 nm. The larger the range of focus, the smaller the pattern dimension change with respect to the change in depth of focus, which is favorable.

(Line Edge Roughness: LER)

With the line pattern of 90 nm obtained by minimum exposure amount to reproduce a line pattern of 90 nm, distance from the standard line where the edge is supposed to exist was measured for 50 points within the range of 2.5 μm edge in the longitudinal direction of the line pattern. Then, standard deviation (σ) was obtained from the measurement result, and the tripled value thereof (3σ) was calculated as LER. When the value is smaller, the roughness becomes smaller and allows achievement of uniform pattern edge, which would be a favorable characteristics.

TABLE 2

|  | resolution | depth of focus | line edge roughness |
|---|---|---|---|
| Ex. 1 | Excellent | Excellent | Good |
| Ex. 2 | Excellent | Excellent | Excellent |
| Ex. 3 | Excellent | Excellent | Excellent |
| Ex. 4 | Excellent | Excellent | Excellent |
| Ex. 5 | Excellent | Excellent | Good |
| Ex. 6 | Excellent | Excellent | Excellent |
| Ex. 7 | Excellent | Excellent | Excellent |
| Ex. 8 | Excellent | Excellent | Excellent |
| Ex. 9 | Excellent | Excellent | Good |
| Ex. 10 | Excellent | Excellent | Excellent |
| Ex. 11 | Excellent | Excellent | Excellent |
| Ex. 12 | Excellent | Excellent | Excellent |
| Comp. Ex. 1 | — | — | — |
| Comp. Ex. 2 | Poor | Poor | Poor |
| Comp. Ex. 3 | Poor | Poor | Poor |
| Comp. Ex. 4 | Poor | Poor | Poor |
| Comp. Ex. 5 | Poor | Poor | Poor |
| Comp. Ex. 6 | Poor | Poor | Poor |
| Comp. Ex. 7 | Poor | Poor | Poor |
| Comp. Ex. 8 | Poor | Poor | Poor |
| Comp. Ex. 9 | Poor | Poor | Poor |
| Comp. Ex. 10 | Poor | Poor | Poor |
| Comp. Ex. 11 | Poor | Poor | Poor |
| Comp. Ex. 12 | Poor | Poor | Poor |

Example 13

Evaluation of Sensitivity

<Preparation of Resist Composition>

Polymer (A-1) as the base polymer (100 parts by mass), trifluoromethanesulfonate=triphenylsulfonium represented by formula (B-5) as the photoacid generator, tellurium containing sulfonium salt 1, and propylene glycol monomethyl ether acetate as the solvent (3000 parts by mass) are mixed, followed by filtration using a PTFE filter, thereby preparing a resist composition (H-25). Details of the resist composition are shown in Table 3.

[Chemical Formula 26]

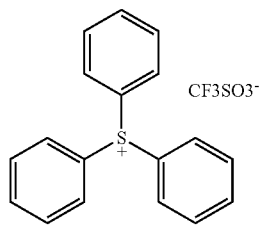

(B-5)

Example 14

Trifluoromethanesulfonate=triphenylsulfonium as the photoacid generator and tellurium containing sulfonium salt 1 are used by the formulation amount shown in Table 3, and the rest of the conditions are carried out in a similar manner as Example 13 to obtain the resist composition (H-26).

Comparative Example 13

A similar procedure as Example 13 is carried out except that tellurium containing sulfonium salt is not added, thereby obtaining the resist composition (H-27). Here, in Examples 13 and 14 and Comparative Example 13, the total molar amount of photoacid generator and tellurium containing sulfonium salt 1 used are the same.

TABLE 3

| resist com-position | polymer type | polymer formulation amount (parts by mass) | photoacid generator formulation amount (parts by mass) | Te containing sulfonium 1 salt formulation amount (parts by mass) | solvent formulation amount (parts by mass) |
|---|---|---|---|---|---|
| Ex. 13 | H-25 | A-1 | 100 | 5.13 | 1.55 | 3000 |
| Ex. 14 | H-26 | A-1 | 100 | 4.40 | 2.72 | 3000 |
| Comp. Ex. 13 | H-27 | A-1 | 100 | 5.87 | — | 3000 |

<Evaluation of Sensitivity>

Each of the resist composition is spin coated on a silicon wafer using a spin coater, followed by pre-baking for 60 seconds at 110° C. on a hot plate, thereby obtaining a coating film having a film thickness of 50 nm. The coating film is exposed by EUV, followed by post-baking for 60 seconds at 110° C. Then, developing is carried out for 60 seconds using a 2.38 mass % aqueous tetramethyl ammonium hydroxide, followed by rinsing with purified water for 30 seconds, thereby obtaining a pattern-formed substrate.

The exposure amount which provides no residual film as the formed resist film is evaluated as the sensitivity.

TABLE 4

| | sensitivity (mJ/cm$^2$) |
|---|---|
| Ex. 13 | 16 |
| Ex. 14 | 8 |
| Comp. Ex. 13 | 20 |

In Examples 1 to 12 which use the tellurium containing sulfonium salt of some of the embodiments of the present invention, characteristics of resolution, depth of focus, and LER are superior. On the other hand, in Comparative Examples 1 to 12 which do not use the tellurium containing sulfonium salt, further improvement is required for the characteristics of resolution, depth of focus, and LER.

Further, as shown Examples 13, 14 and Comparative Example 13, in the evaluation of sensitivity, it can be understood that sensitivity can be enhanced by adding a suitable amount of tellurium containing sulfonium salt to photoacid generator. Here, when either one of the photoacid generators (B-1) to (B-4) is used in combination with the tellurium containing sulfonium salt in place of photoacid generator represented by formula (B-5) as the photoacid generator, a similar result as Examples 13 and 14 can be achieved.

From the afore-mentioned results, the photosensitive compound according to one of the embodiments of the present invention have superior sensitivity, resolution, and depth of focus in lithography, and has an effect to suppress LER in fine pattern.

The invention claimed is:

1. A resist composition comprising:

a photoacid generator; and a compound including a protecting group to be deprotected by acid, wherein: the photoacid generator contains a skeleton selected from the group consisting of an onium salt skeleton, a diazomethane skeleton, an imide skeleton and an oxime skeleton; and the skeleton comprises a Te atom containing group represented by the following formula (1):

$$*-Te-R^1 \qquad (1)$$

where in the formula (1), each of $R^1$ is independently selected from the group consisting of a linear, branched, or cyclic hydrocarbon group having 2 to 20 carbon atoms, and an aryl group having 5 to 20 carbon atoms;

the linear hydrocarbon group is selected from the group consisting of ethyl, n-propyl and n-butyl;

a part of or all of hydrogen atoms of the hydrocarbon group and the aryl group can be substituted by a first substituent group;

when the hydrocarbon group includes at least one methylene group, a group including a divalent hetero atom can be included in place of the at least one methylene group;

the aryl group can include a hetero atom in place of at least one carbon atom in a cyclic structure; and

* represents a bonding portion with the skeleton.

2. The resist composition of claim 1, wherein the photoacid generator is represented by the following formula (2):

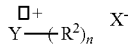  (2)

where in the formula (2), Y represents an atom selected from the group consisting of an iodine atom, a sulfur atom, a selenium atom, and a tellurium atom;

when Y is the iodine atom, n is 2;

when Y is either one selected from the group consisting of the sulfur atom, the selenium atom, and the tellurium atom, n is 3;

$R^2$ is independently selected from each other from the same candidates for the $R^1$, and at least one of $R^2$ contains the Te atom containing group as a second substituent group in place of at least one hydrogen atom;

two or more of $R^2$ can be bonded to each other to form a ring structure with Y, the ring structure can include a hetero atom; and X" represents an anion.

3. The resist composition of claim 1, further comprising a second photoacid generator.

4. A method for manufacturing a device comprising:
forming a resist film on a substrate by using the resist composition of claim 1;
exposing the resist film carried out by using electron beam or extreme ultraviolet; and
forming a resist pattern by developing the exposed resist film.

5. The resist composition of claim 1,
wherein: the onium salt skeleton has a cation atom selected from the group consisting of an iodine atom, a sulfur atom, a selenium atom, and a tellurium atom; and
the imide skeleton is represented by the following formula (3):

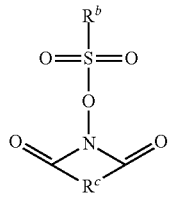  (3)

where in the formula (3), at least one of $R^b$ and $R^C$ includes the Te atom containing group in the formula (1);

$R^b$ represents a group selected from the group consisting of: an alkyl group having 1 to 8 carbon atoms; an alkenyl group having 2 to 8 carbon atoms; an alkoxyalkyl group having 1 to 8 carbon atoms; and an aryl group;

a part of or all of hydrogen atoms of $R^b$ can be substituted with a third substituent group;

$R^C$ represents a group selected from the group consisting of: an arylene group having 6 to 10 carbon atoms; an alkylene group having 1 to 6 carbon atoms; and an alkenylene group having 2 to 6 carbon atoms; and a part of or all of hydrogen atoms of RC can be substituted with a fourth substituent group.

* * * * *